United States Patent
Yoon et al.

(10) Patent No.: US 10,542,945 B2
(45) Date of Patent: Jan. 28, 2020

(54) X-RAY IMAGING APPARATUS AND CONTROL METHOD FOR THE SAME

(71) Applicant: Samsung Electronics Co., Ltd., Gyeonggi-do (KR)

(72) Inventors: Hyung-Won Yoon, Seoul (KR); Su Young Ko, Gyeonggi-do (KR); Tae Kyun Kim, Seoul (KR); Jin-Ho Choi, Gyeonggi-do (KR); Hyung Sok Yeo, Gyeonggi-do (KR); Jun Young Lee, Gyeonggi-do (KR)

(73) Assignee: Samsung Electronics Co., Ltd., Samsung-ro, Yeongtong-gu, Suwon-si, Gyeonggi-do (KR)

( * ) Notice: Subject to any disclaimer, the term of this patent is extended or adjusted under 35 U.S.C. 154(b) by 483 days.

(21) Appl. No.: 15/202,012

(22) Filed: Jul. 5, 2016

(65) Prior Publication Data
US 2017/0042491 A1    Feb. 16, 2017

(30) Foreign Application Priority Data
Aug. 10, 2015    (KR) .......................... 10-2015-0112306

(51) Int. Cl.
*A61B 6/00*    (2006.01)
*A61B 6/04*    (2006.01)
*A61B 6/02*    (2006.01)

(52) U.S. Cl.
CPC ............ *A61B 6/0414* (2013.01); *A61B 6/025* (2013.01); *A61B 6/502* (2013.01)

(58) Field of Classification Search
CPC ........ A61B 6/502; A61B 6/025; A61B 6/0414
See application file for complete search history.

(56) References Cited

U.S. PATENT DOCUMENTS

| 5,335,257 A | 8/1994 | Stunberg | |
|---|---|---|---|
| 2005/0008117 A1* | 1/2005 | Livingston | ........... A61B 6/0414 378/37 |
| 2014/0177791 A1* | 6/2014 | Otokuni | ............... A61B 6/0414 378/37 |

FOREIGN PATENT DOCUMENTS

| JP | 2011-206434 A | 10/2011 |
|---|---|---|
| JP | 2011-206438 A | 10/2011 |
| JP | 2014-57901 A | 4/2014 |
| JP | 2014-124364 A | 7/2014 |

* cited by examiner

*Primary Examiner* — Dani Fox
(74) *Attorney, Agent, or Firm* — Cha & Reiter, LLC

(57) ABSTRACT

An X-ray imaging method and an apparatus having an improved structure configured to reduce pain and discomfort during a procedure. The X-ray imaging apparatus acquires an X-ray image by compressing an object that is irradiated by an X-ray source. An X-ray detector includes an object contact material that contacts the object. X-rays that pass through the object are detected X-rays, an electrical signal is generated based on the X-rays. A paddle is disposed between the X-ray source and the X-ray detector to be vertically adjustable relative to the X-ray source and X-ray detector so as to compress the object placed on the object contact surface. The paddle includes a supporting member, a pressure member coupled to the supporting member, and at least one adjustment member arranged between the supporting member and the pressure member to regulate movement of the pressure member according to the shape of the object.

18 Claims, 27 Drawing Sheets

X-RAY IMAGING APPARATUS AND CONTROL METHOD FOR THE SAME

CLAIM OF PRIORITY

This application claims the benefit of priority from Korean Patent Application No. 2015-0112306, filed on Aug. 10, 2015 in the Korean Intellectual Property Office, the disclosure of which is incorporated herein by reference.

BACKGROUND

1. Field of the Disclosure

Embodiments of the present disclosure relate to an X-ray imaging apparatus and a control method thereof, more particularly the X-ray imaging apparatus having an improved structure configured to reduce the pain and/or discomfort felt by a patient during an X-ray procedure, and a control method for the same.

2. Description of Related Art

X-ray imaging apparatuses are apparatuses configured to irradiate an object with X-rays to an object and obtain an internal image of the object using the X-rays that passed through the object. Since transmittance of X-rays differs based on characteristics of a material(s) forming the object, it is possible to detect the intensity or strength of the X-rays that passed through the object to generate an image of an internal structure of the object.

In the field of X-ray imaging apparatuses, an apparatus particularly configured to examine the breasts is referred to as a mammogram machine. One of the issues concerning performing a mammography properly is that the that the human breast has both breast tissue and fat tissue, and thus it is necessary to perform X-ray imaging while compressing the breast, which is located between an X-ray source and an X-ray detector, so as to acquire an X-ray image displaying the internal structure of the breast clearly.

During compressing the breast by the paddle for the X-ray image, the breast may be overly-compressed. Excessive compression of the breast may cause the patient to feel pain or discomfort. Therefore, there is a need in the art to provide a method and apparatus to prevent the excess compression of the breast so that the patient may take an X-ray imaging procedure in a relaxed state without pain or discomfort.

SUMMARY

Therefore, it is an aspect of the present disclosure to provide an X-ray imaging apparatus having an improved structure configured to apply a compression force to an object evenly, and a control method for the same.

It is another aspect of the present disclosure to provide an X-ray imaging apparatus having an improved structure configured to reduce pain and discomfort, which may be given to a patient during an X-ray imaging procedure, and a control method for the same.

Additional aspects of the present disclosure will be set forth in part in the description which follows and, in part, will be understood by an artisan based on reading the description, or may be learned by practice of the appended claims.

In accordance with an aspect of the present disclosure, an X-ray imaging apparatus is configured to acquire an X-ray image by compressing an object includes an X-ray source, an X-ray detector, and a paddle. The X-ray source may generate X-rays that irradiate the object. The X-ray detector may include an object contact unit comprised of a material that is preferable resistant to X-rays. The contact unit is configured to make contact with the object, and the X-ray detector may detect X-rays passed through the object and convert the detected X-rays into an electrical signal. The paddle may be disposed between the X-ray source and the X-ray detector to be vertically adjustable relative to the X-ray source and X-ray detector so as to compress the object placed on the object contact unit. The paddle may include a supporting member, a pressure member coupled to the supporting member to compress the object, and at least one adjustment member disposed between the supporting member and the pressure member to regulate the movement of the pressure member according to the shape of the object, when the pressure member compresses the object.

The at least one adjustment member may regulate the movement of the pressure member by using an elastic force.

The pressure member may perform at least one motion of yawing motion of rotation with respect to a first axis in parallel with an elevation direction of the paddle, rolling motion of rotation with respect to a second axis perpendicular to the first axis to face the object, and pitching motion of rotation with respect to a third axis perpendicular to the first axis and the second axis.

The at least one adjustment member may connect the pressure member to the supporting member so that the pressure member performs at least one motion of pitching motion, rolling motion, and yawing motion.

The supporting member may include a plurality of arms disposed to face both opposite sides of the pressure member, and provided with a rotary shaft, which is formed to be protruded toward of the inside of the paddle so that the pressure member performs a rotary movement while being coupled thereto.

The at least one adjustment member may include a first elastic member configured to connect the pressure member and the plurality of arms to be tension in a rotary direction of the pressure member.

In the plurality of arms, an interference protrusion may be provided to be protruded in the direction of the paddle (e.g. inward of the paddle) substantially in parallel with the rotary shaft, wherein the interference protrusion may be inserted into an interference hole that is formed on the opposite sides of the pressure member facing the plurality of arms, the interference protrusion limits the rotary movement of the pressure member.

The at least one adjustment member may include a second elastic member configured to wind the rotary shaft, wherein one end portion of the second elastic member may be fixedly coupled to the plurality of arms, and the other end portion of the second elastic member may be fixedly coupled to the pressure member.

On opposite sides of the pressure member facing the plurality of arms, a shaft coupling hole may be formed to be long in an elevation direction of the paddle so that the rotary shaft is moved while being inserted thereinto, and the at least one adjustment member may include a third elastic member provided in a lower side of the rotary shaft to support the rotary shaft.

The pressure member may include an installation frame coupled to one surface of the pressure member facing the supporting member to be moved together with the pressure member, and the at least one adjustment member may be disposed between the installation frame and the supporting member to connect the installation frame and the supporting member.

The at least one adjustment member may include at least one of rubber, and silicon.

The at least one adjustment member may include a first coupling unit facing the installation frame, and a second coupling unit facing the supporting member, wherein a first fixing member, which is penetrably coupled to the installation frame, may be coupled to the first coupling unit, and a second fixing member, which is penetrably coupled to the supporting member, may be coupled to the second coupling unit.

The pressure member may include a slit formed along at least one side of the pressure member to allow the pressure member to be elastically deformed when an external force is applied to the pressure member.

The pressure member may further include a slit cover detachably coupled to the slit and having an elastic material.

The pressure member may include an object compression surface compressing the object, and a corresponding surface facing the object compression surface wherein an opening unit configured to be communicated with an inner space of the pressure member may be formed on a portion of the corresponding surface.

In accordance with another aspect of the present disclosure, an X-ray imaging apparatus includes a paddle configured to be raisable to compress an object during an X-ray procedure of the object. The paddle may include a pressure member configured to compress the object, and at least one elastic member configured to regulate the movement of the pressure member by using the elastic force so as to compress the object evenly when the pressure member compresses the object.

The at least one elastic member may include at least one of spring, rubber and silicon.

The pressure member may perform at least one motion of yawing motion of rotating with respect to a first axis in parallel with an elevation direction of the paddle, rolling motion of rotating with respect to a second axis perpendicular to the first axis to be toward the object, and pitching motion of rotating with respect to a third axis perpendicular to the first axis and the second axis.

The paddle may further include a supporting member provided with at least one elastic member between the pressure member.

The pressure member may be rotatably-coupled via a hinge to the supporting member.

The at least one elastic member may be disposed on a lateral side of the pressure member to connect the pressure member to the supporting member.

The supporting member may include a plurality of arms disposed to face opposite sides of the pressure member, and provided with a rotary shaft, which is formed to be protruded toward the inside of the paddle so that the pressure member performs a rotary movement while being coupled thereto.

The at least one elastic member may connect the pressure member and the plurality of arms to be tension in a rotary direction of the pressure member.

The at least one elastic member may include a first elastic unit installed in a lateral side of the pressure member, and a second elastic unit installed in another lateral side of the pressure member to correspond to the first elastic unit, and the elastic units comprised in part by an elastomeric material. The first elastic unit and the second elastic unit may be independently tensioned so that the pressure member may apply uniform compression force according to the shape of the object.

In the plurality of arms, an interference protrusion may extend toward the inside of the paddle substantially in parallel with the rotary shaft, and wherein the interference protrusion may be inserted into an interference hole, which is formed on the opposite sides of the pressure member facing the plurality of arms, to limit the rotary movement of the pressure member.

The at least one elastic member may be disposed on a rear side of the pressure member to connect the pressure member to the supporting member when a direction toward the object represents a front side of the pressure member.

The pressure member may include a slit formed along at least one side of the pressure member to allow the pressure member to be elastically deformed when an external force is applied to the pressure member, and a slit cover detachably coupled to the slit and having an elastic material.

The pressure member may include an object compression surface compressing the object, a corresponding surface facing the object compression surface, and a plurality of connection surfaces connecting the object compression surface to the corresponding surface, wherein an opening unit configured to be communicated with an inner space of the pressure member may be formed on at least one of the corresponding surface and the plurality of connection surfaces.

In accordance with another aspect of the present disclosure, a I method of controlling an X-ray imaging apparatus configured to acquire an X-ray image by compressing an object includes lowering a paddle to compress the object, measuring a thickness of the object compressed by the paddle, comparing the thickness of the object with a reference thickness in an imaging condition table, and raising the paddle to compress the object less when the reference thickness is thicker than the thickness of the object.

BRIEF DESCRIPTION OF THE DRAWINGS

These and/or other aspects of the disclosure will become apparent and more readily appreciated by a person of ordinary skill in the art from the following description of embodiments, taken in conjunction with the accompanying drawings of which.

DETAILED DESCRIPTION

Hereinafter embodiments of an X-ray imaging apparatus and a control method thereof will be described with reference to the accompanying drawings. In the following detailed description, the terms of "front end", "rear end", "upper portion", "lower portion", "upper end", "lower end" and the like may be defined by the drawings, but the shape and the location of the component is not limited by the term.

Figure 1:
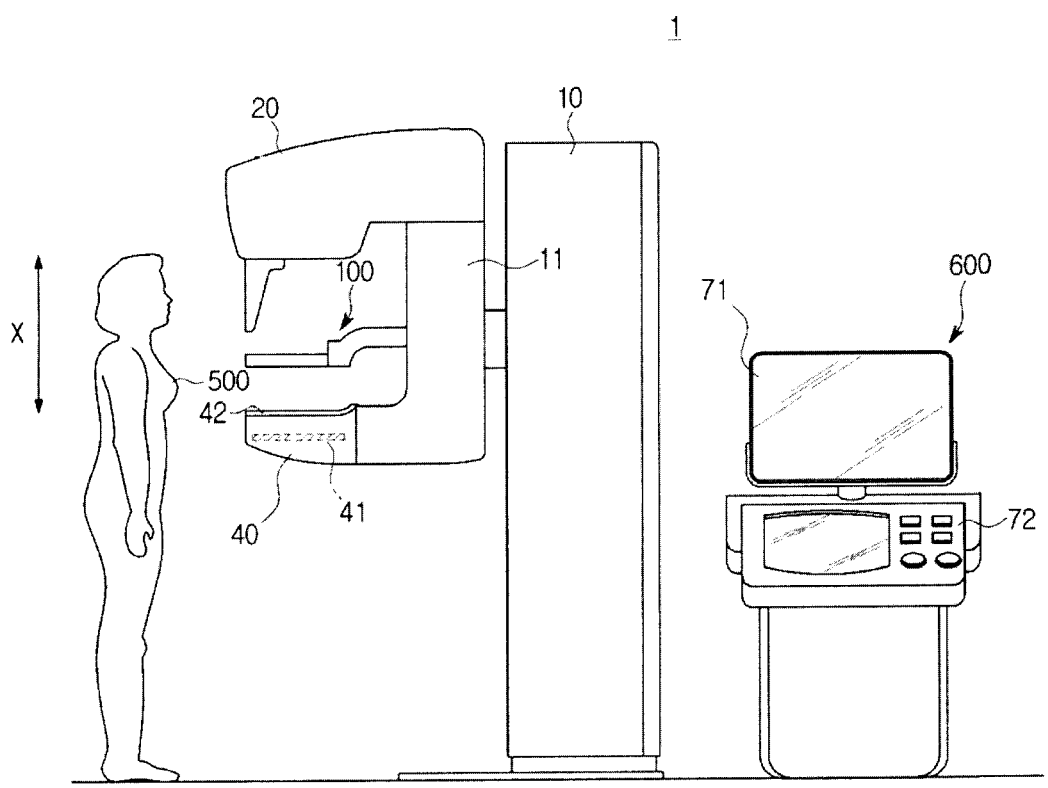
FIG. 1 is a view schematically illustrating an exterior of an X-ray imaging apparatus in accordance with an embodiment of the present disclosure.

FIG. 1 is a view schematically illustrating an exterior of an X-ray imaging apparatus in accordance with an embodiment of the present disclosure.

As illustrated in FIG. 1, an X-ray imaging apparatus 1 for breast X-ray imaging (i.e. a mammography machine) may have a specialized structure to image the breast in comparison with a general X-ray imaging apparatus. Particularly, in the case where an X-ray source 20 and an X-ray detector assembly 40 may be mounted to a gentry 10, X-rays may be irradiated onto an object 500 placed between the X-ray source 20 and the X-ray detector assembly 40, and an X-ray image of the object 500 may be acquired by detecting the X-rays passed through the object 500. In embodiments of the present disclosure, the object 500 may be a patient's breast. Hereinafter the term "object" may be used interchangeably with "breast".

An X-ray imaging apparatus 1 may further include a paddle 100 disposed between the X-ray source 20 and the X-ray detector assembly 40. The paddle 100 may be provided to compress the object 500 placed on an object contact unit 42. A detail description of the paddle 100 will be described later.

Figure 2:
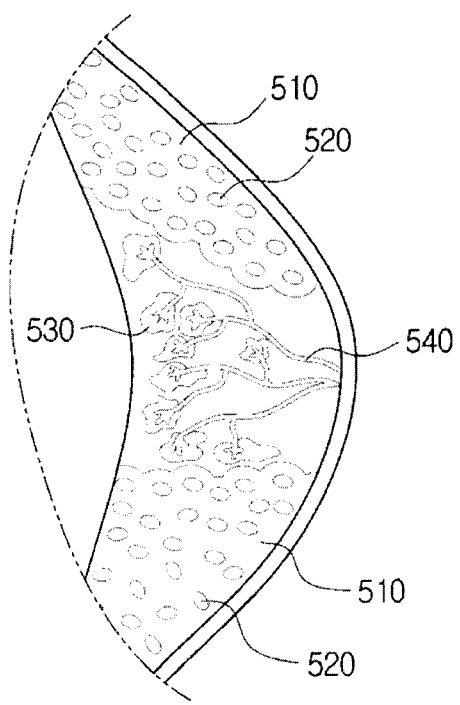
FIG. 2 is a cross-sectional view schematically illustrating an internal structure of a breast available for imaging by an X-ray imaging apparatus in accordance with an embodiment of the present disclosure.
Figure 3:
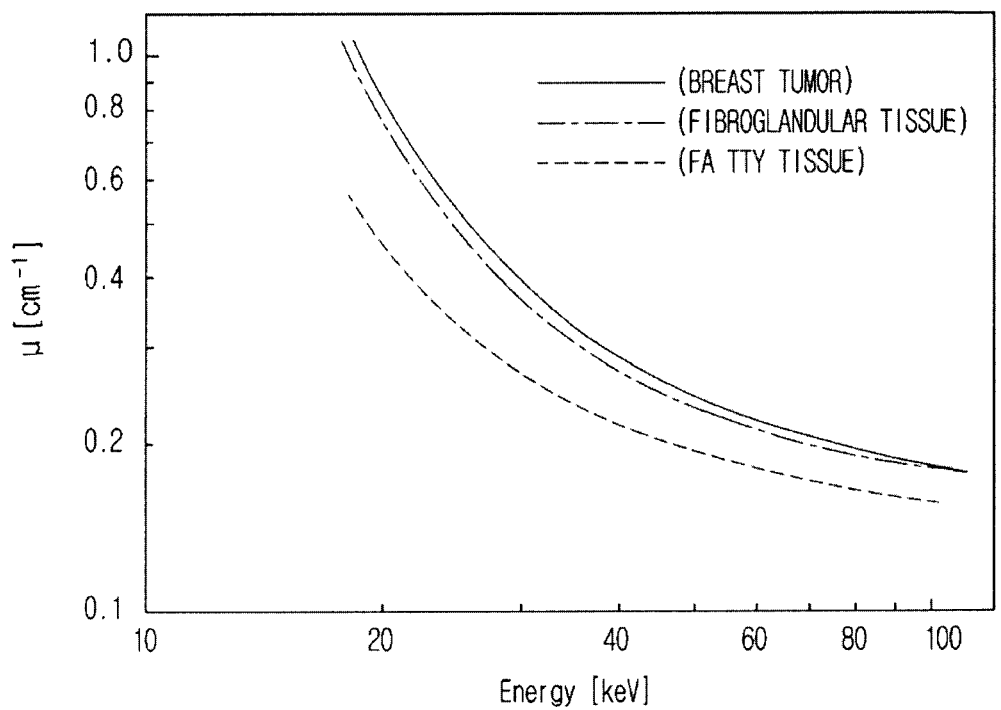
FIG. 3 is a graph illustrating attenuation coefficient of materials composing the breast of FIG. 2.

FIG. 2 is a cross-sectional view schematically illustrating an internal structure of the breast available for imaging by an X-ray imaging apparatus in accordance with an embodiment of the present disclosure and FIG. 3 is a graph illustrating attenuation coefficient of materials composing the breast of FIG. 2.

As illustrated in FIGS. 2 and 3, the structure of the breast 500 includes a fibrous tissue 510 that surrounds the circumference of the breast and supports the shape of the breast, a fatty tissue 520 distributed in the entire breast, a breast tissue (lobes) 530 producing the breast milk, and a mammary gland tissue (ducts) 540 in which the breast milk is passed through. Among those, a structure related to the production and the supply of the breast milk, e.g. the breast tissue 530 and the mammary gland tissue 540 may be referred to as fibroglandular tissue.

Attenuation coefficient is data to describe the extent to which the radiant flux of X-ray is reduced as it passes through a specific material. Since attenuation coefficient varies depending on each material composing the inside of the object 500 and thus it may be possible to image the inside of the object 500 by penetrating X-rays. FIG. 3 illustrates an attenuation coefficient corresponding to energy band of a breast tumor, a fibroglandular tissue, and a fatty tissue composing the breast. As illustrated in FIG. 3, there are little differences between attenuation coefficients of each material composing the breast. The reason is that, as illustrated in FIG. 2, the breast is only composed of soft tissue, and thus the technician or apparatus may be required to compress the breast using the paddle 100 to acquire as clear X-ray image as possible. In addition, when compressing the breast, a thickness of the object is reduced and the exposure of X-ray may be reduced.

Referring to FIG. 1 again, with regard to the X-ray imaging, when the breast 500 is placed on the object contact unit 42, the paddle 100 may compress the breast 500, the X-ray source 20 may emit X-rays to the compressed breast 500, and then an X-ray detector 41 may detect X-rays penetrated through the breast 500 thereby acquiring an X-ray image of the breast 500.

There are some elements, which are temperature-sensitive among the elements constituting the X-ray imaging apparatus 1. Particularly, the X-ray detector 41 is temperature-sensitive because of including a semiconductor element, and thus if not keeping the temperature suitable for the characteristics of the element, the element may be not operate properly, thus causing an error. Therefore, a scan room in which the X-ray imaging apparatus 1 is placed, and the X-ray imaging apparatus 1 itself may be kept at a proper temperature that is suitable for the characteristics of the element.

Figure 4:
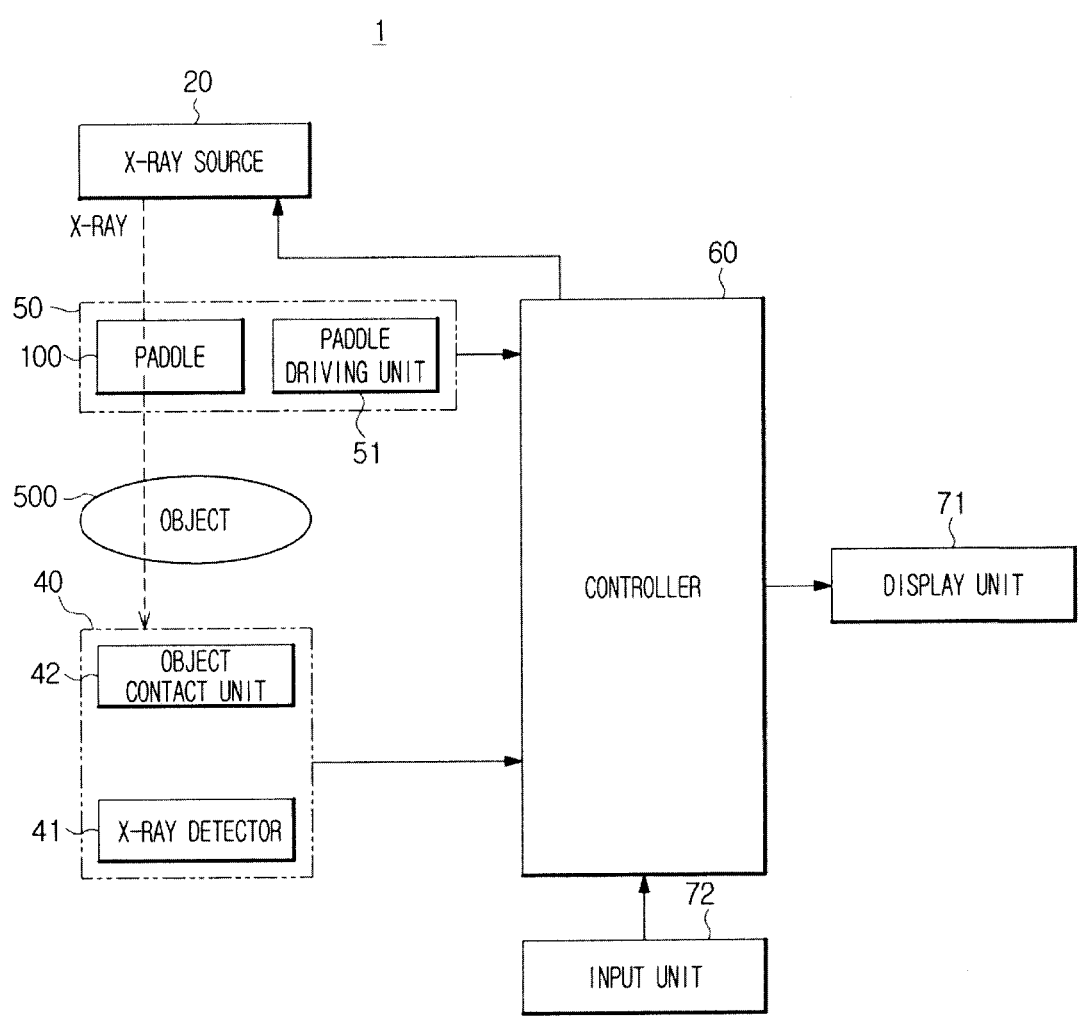
FIG. 4 is a control block diagram illustrating an X-ray imaging apparatus in accordance with an embodiment of the present disclosure.
Figure 5A:
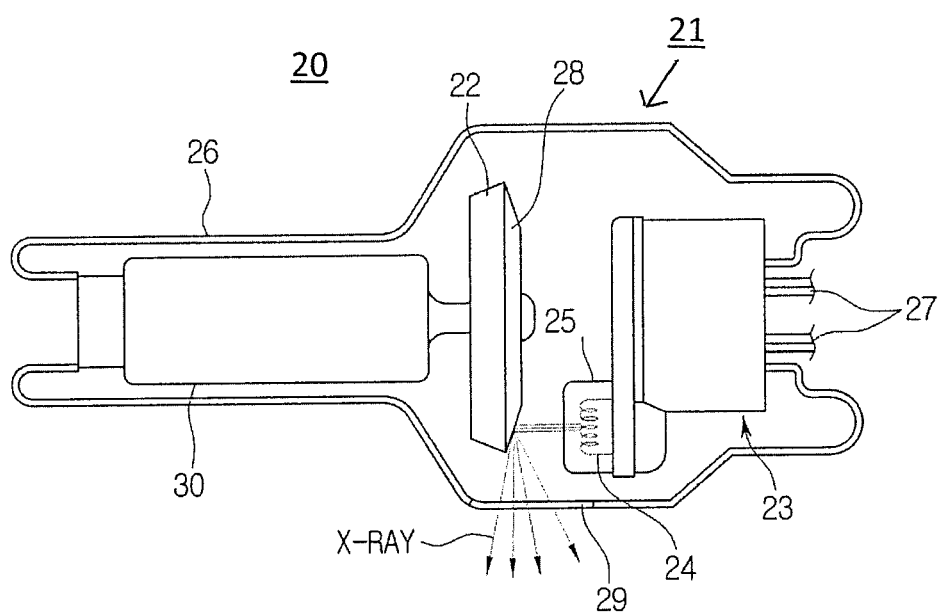
FIG. 5A is a cross-sectional view schematically illustrating an internal structure of an X-ray source of an X-ray imaging apparatus in accordance with an embodiment of the present disclosure.
Figure 5B:
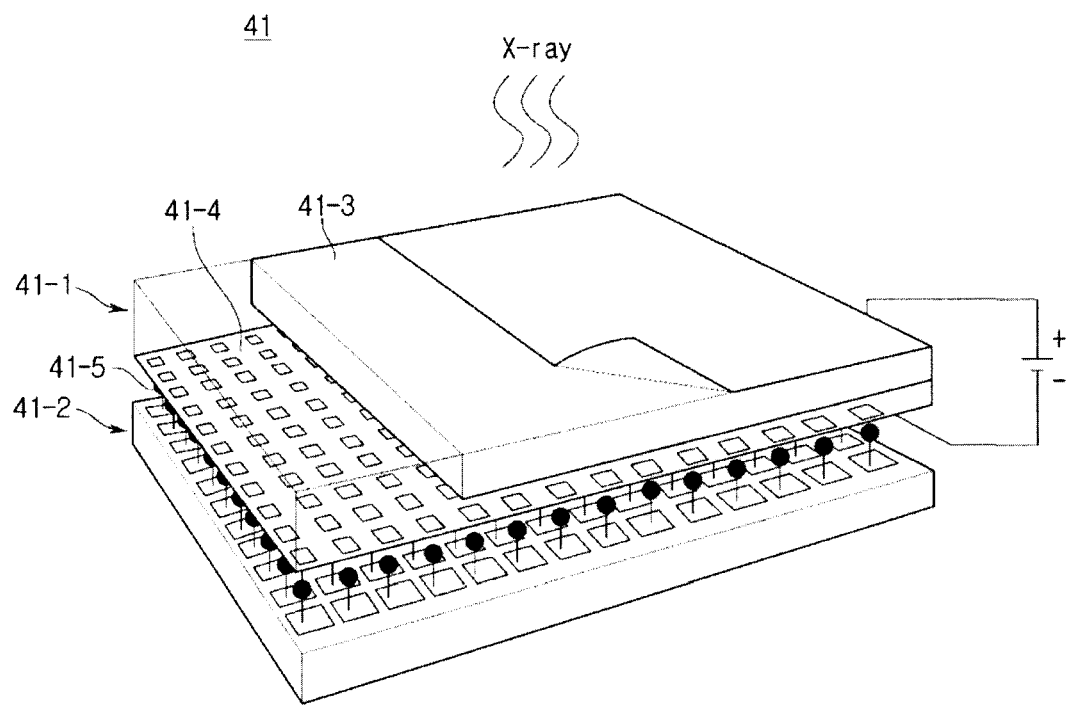
FIG. 5B is a perspective view schematically illustrating a configuration of an X-ray detector of an X-ray imaging apparatus in accordance with an embodiment of the present disclosure.

FIG. 4 is a control block diagram illustrating an X-ray imaging apparatus in accordance with an embodiment of the present disclosure, FIG. 5A is a cross-sectional view schematically illustrating an internal structure of an X-ray source of an X-ray imaging apparatus in accordance with an embodiment of the present disclosure, and FIG. 5B is a perspective view schematically illustrating a configuration of an X-ray detector of an X-ray imaging apparatus in accordance with an embodiment of the present disclosure.

As illustrated in FIG. 4, the X-ray imaging apparatus 1 may include the X-ray source 20 configured to generate X-rays that irradiate onto the object 500, the X-ray detector assembly 40 configured to detect X-rays passed through the object 500, a paddle assembly 50 configured to compress the object 500, a controller 60 comprising hardware such as at least one processor, microprocessor or microcontroller configured to control an operation of the X-ray imaging apparatus 1, a display unit configured to display an X-ray image, and an input unit configured to input a control command related to the operation of the X-ray imaging apparatus 1.

The X-ray source 20 may generate X-rays by receiving power from a power supply unit, the energy of the X-rays may be regulated by a tube voltage, and the intensity and dose of the X-rays may be controlled by tube current and X-ray exposure time.

As illustrated in FIG. 5A, the X-ray source 20 may include an X-ray tube 21 configured to generate X-rays, and the X-ray tube 21 may be realized in a two-pole vacuum tube including the anode 22 and the cathode 23. The cathode 23 may include filaments 24 and a focusing electrode 25 configured to focus electrons. The focusing electrode 25 may be referred to as a focusing cup.

The inside of a glass tube 26 may become approximately 10 mmHg of a high vacuum state therein and the filament 24 of the cathode 23 may be heated by a high temperature so that hot electrons may be generated. A tungsten filament may be used as the filament 24, and the filament 24 may be heated by applying a current to an electrical conductor 27 connected to the filament.

The anode 22 may be mainly composed of copper, and a target material 28 may be applied or placed on a side facing the cathode 23. The target material may include high resistance materials, such as Cr, Fe, Co, Ni, W, and Mo. The melting point of the target material may be higher, as a focal spot size is reduced. The focal spot may represent an effective focal spot. In addition, the target material may be inclined with a certain angle. Thus an inclined angle may be smaller as the focal spot size decreases.

When a high voltage is applied to between the cathode 23 and the anode 22, hot electron may be accelerated and collided with the target material 28 of the anode thereby generating X-rays. The generated X-rays may be irradiated to the outside through a window 29 and the window 29 may include beryllium (Be) thin film. At this time, a filter may be disposed on the front surface or the rear surface of the window 29 to filter X-rays in a certain energy bands.

The target material 28 may be rotated by a rotor 30. When the target material 28 is rotated, the heat accumulation rate may be increased more than 10 times per unit area and the size of the focal point may be reduced as compared to when the target material 28 is fixed.

A voltage applied between the cathode 23 and the anode 22 of the x-ray tube 21 may be referred to as a tube voltage, and a size of the tube voltage may be represented by a peak value (kvp). When the tube voltage is increased, a speed of the hot electrons may be increased, and thus an X-ray energy (a photon energy), which is generated by colliding with the target material 28, may be increased. A current flowing through the X-ray tube 21 may be referred to as a tube current and the tub current may be represented by an average value (mA). When the tube current is increased, the number of hot electrons emitted from the filament may be increased and thus the dose of X-ray (the number of X-ray photons), which is generated by colliding with the target material 28, may be increased.

Therefore, the X-ray energy may be controlled by the tube voltage, and the strength or the dose of X-rays may be controlled by the tube current and the X-ray exposure time. Particularly, when the irradiated X-rays have a predetermined energy band, the energy band may be defined by upper and lower limits. The upper limit of the energy band, i.e. the maximum energy of the irradiated X-rays may be adjusted by the size of the tube voltage, and the lower limit of the energy band, i.e., the minimum energy of the irradiated X-ray may be adjusted by the filter. When the X-rays of low energy band are filtered by using the filter, the average energy of the irradiated X-rays may be increased.

The X-ray detector assembly 40 may be referred to as "bucky" and may include the object contact unit 42 to which an object is contacted, and the X-ray detector 41 configured to detect X-rays.

The X-ray detector 41 may detect X-rays passed through the object, and may acquire an image signal by converting the detected X-rays into an electrical signal. The image signal may represent a signal indicating the intensity of the incident X-rays per pixel, and the image signal may be outputted to the controller 60. The controller 60 may generate an X-ray image of the object using the image signal.

In general, the X-ray detector 41 may be classified based on a material composition method, a method for converting the detected X-rays to an electrical signal and a method for obtaining an image signal.

First, the X-ray detector 41 may be divided into a case where it is formed of a single element and a case where it is formed of composite elements, based on the material composition method.

In the case the X-ray detector 41 is formed of a single material, a section that detects the X-rays and generates an electrical signal and a section that reads and processes the electrical signal may be formed of a semiconductor of a single material or may be manufactured with a single process, e.g. using a Charge Coupled Device (CCD) or a Complementary Metal Oxide Semiconductor (CMOS).

In the case the X-ray detector 41 is formed of composite elements, a section that detects the X-ray and generates an electrical signal and a section that reads and processes the electrical signal may be formed of different materials or manufactured with different processes. For example, there may be an occasion where photo detectors, such as e.g., photo diodes, CCD, CdZnTe, etc., are used to detect an X-ray and CMOS Read Out Integrated Circuits (ROICs) are used to read and process the electric signal; an occasion where strip detectors are used to detect X-rays and the CMOS ROICs are used to read and process the electrical signal; and an occasion where a-Si or a-Se flat panel systems are used.

Furthermore, the X-ray detector may be divided into a direct conversion method and indirect conversion method based on the method for converting the X-ray to an electrical signal.

In the direct conversion method, when X-rays are irradiated, an electron-hole and hole may be generated temporarily inside the photodetector, and the electron to may be moved to the positive electrode and the hole may be moved to the negative electrode by an electrical field applied to opposite ends of the photodetector. The X-ray detector may convert the movements into an electrical signal. In the direct conversion method, a material used for the photodetector may be a-Se, CdZnTe, HgI2, PbI2, etc.

In the indirect conversion method, in a state in which a scintillator is provide between photodetector and the X-ray source, the X-rays irradiated from the X-ray source may react with a scintillator to cause photons having a visible wavelength in a visible spectrum to be emitted, and the photodetector may detect the photons and generate an electrical signal. The material used for the photodetector in the indirect conversion method may be e.g., a-Si, and the scintillator may be GADOX scintillator in the form of a thin film, or a micro column type or needle structure type CSI (T1).

Based on the method for obtaining the electric signal, the X-ray detector may be divided into charge integration mode for storing charges for a certain period of time and obtaining a signal from the charges, and photon counting mode for counting the number of photon having energy more than threshold energy whenever a signal is generated by a single X-ray photon.

In embodiments of the present disclosure, there is no limit in a material composition method, a method for converting the detected X-rays to an electrical signal and a method for obtaining an image signal of the X-ray detector 41, and thus any type of method from among the above-mentioned method may be applied to the X-ray detector 41. In addition, the present disclosure is not limited thereto, and thus any type of method configured to detect X-rays, to "convert" the detected X-ray into an electrical signal, and to acquire an image signal may be applied.

Hereinafter the X-ray detector 41, to which the direct conversion method configured to acquire an electrical signal from X-rays directly, and a hybrid method in which a photodetector configured to detect X-rays is coupled to a read out circuit chip are applied, will be described.

As illustrated in FIG. 5B, the X-ray detector 41 may include a photodetector 41-1 that receives the detected X-rays and generates an electrical signal and a readout circuit 41-2 reading the electrical signal. The read-out circuit 41-2 may be formed in a two-dimensional pixel array including a plurality of pixel regions. The photodetector 41-1 may be composed of a single crystal semiconductor material, such as Ge, CdTe, CdZnTe, GaA, in order to ensure high resolution, fast response time and high dynamic range in a low energy and a low dose.

The photodetector 41-1 may be formed in a PIN photodiode in which a p-type layer 41-4 in which a p-type semiconductor is arranged in a two-dimensional pixel is boned to at a lower portion of a n-type semiconductor substrate of high resistance 41-3. The read circuit 41-2 using CMOS processes may be coupled to the photodetector 41-1 for each pixel. The CMOS readout circuit 41-2 and the photodetector 41-1 may be coupled to each other in a flip chip bonding method, particularly may be coupled to each other in such a way of forming bump 41-5, such as solder (PbSn), indium (In), reflowing and pressuring by applying heat.

However, the above-described structure is only one example of the X-ray detector 41, but is not limited thereto.

The paddle assembly 50 may include a paddle 100 configured to compress the breast, and a driving unit 51 configured to drive the paddle 100. At least one portion of the paddle 100 may be formed of transparent material, which does not have any effect on the penetration of the X-rays. The paddle driving unit 51 may include a gear or a motor so that the paddle 100 may be manually or automatically moved and fixed. A detail description of the paddle 100 will be described later.

With reference to FIGS. 1 and 4 to 5B, a detail operation of the X-ray imaging apparatus 1 will be described.

As illustrated in FIGS. 1 and 4 to 5B, the X-ray source 20, the X-ray detector assembly 40 and the paddle 100 may be connected to a frame 11 configured to support the X-ray source 20, the X-ray detector assembly 40 and the paddle 100, and the frame 11 may be mounted to the gentry 10. As mentioned above, X-rays may be generated by supplying power to the X-ray tube 21, and thus a high voltage generator may be provided in the gentry 10 so as to supply high voltage to the X-ray tube 21.

The paddle 100 may be movable up and down along the frame 11, and the paddle driving unit 51 configured to drive the paddle 100 may be mounted to the inside of the frame 11. For the X-ray imaging, the patient may place her breast 500 on the object contact unit (i.e. contact surface) 42. At this time, the X-ray detector assembly 40 may play a role of supporting the object 500. The object contract unit 42 may be formed of a material, which minimizes the absorption of the X-rays, such as carbon. Thus, carbon may be used to form the object contact unit 42.

In addition, the paddle 100 may compress the breast (i.e. "object") 500 to have a proper thickness for the X-ray imaging. The paddle 100 may be regulated manually by a user or regulated automatically based on a predetermined value. For example, when a thickness of the object 500 is set as 5 cm for the X-ray imaging, the controller 60 may transmit a control signal to the paddle driving unit 51 so that the paddle 100 may be moved to a position spaced apart from the object contact unit 42 by 5 cm.

With continued reference to FIG. 4, when performing the X-ray imaging, a part to which the breast 500 makes contact may be the object contact unit 42 and a lower portion of the paddle 100. As mentioned above, the X-ray detector 41 may include a semiconductor element. Accordingly, the X-ray detector 41 may be temperature-sensitive, and thus the component of the X-ray imaging apparatus 1 including the X-ray detector assembly 40 may be kept at a low temperature to ensure proper operation.

The controller 60, which includes hardware such as at least one processor or microprocessor having circuitry configured for operation, may control the entire operation of the X-ray imaging apparatus 1, or it can be divided among multiple processors. Therefore, the controller 60 may generate an X-ray image by receiving X-ray data from the X-ray detector 41, may control the generation and the irradiation of the X-rays in the X-ray source 20, and may regulate the movement of the paddle 100.

The X-ray imaging apparatus 1 may include a host device 600 (FIG. 1) as a main control device. The host device 600 may be referred to as "workstation" or "console". The host device 600 may include a display unit 71, which plays as a user interface and displays an X-ray image and a screen related to the control of the X-ray imaging apparatus 1, and an input unit 72 configured to receive an input of a control command from a user.

Since the controller 60 is not limited to a single physical module, a module to perform a part of operation may be provided in the host device 600, and another module to perform another part of operation may be provided in the gentry 10 and the frame 11.

Figure 6:
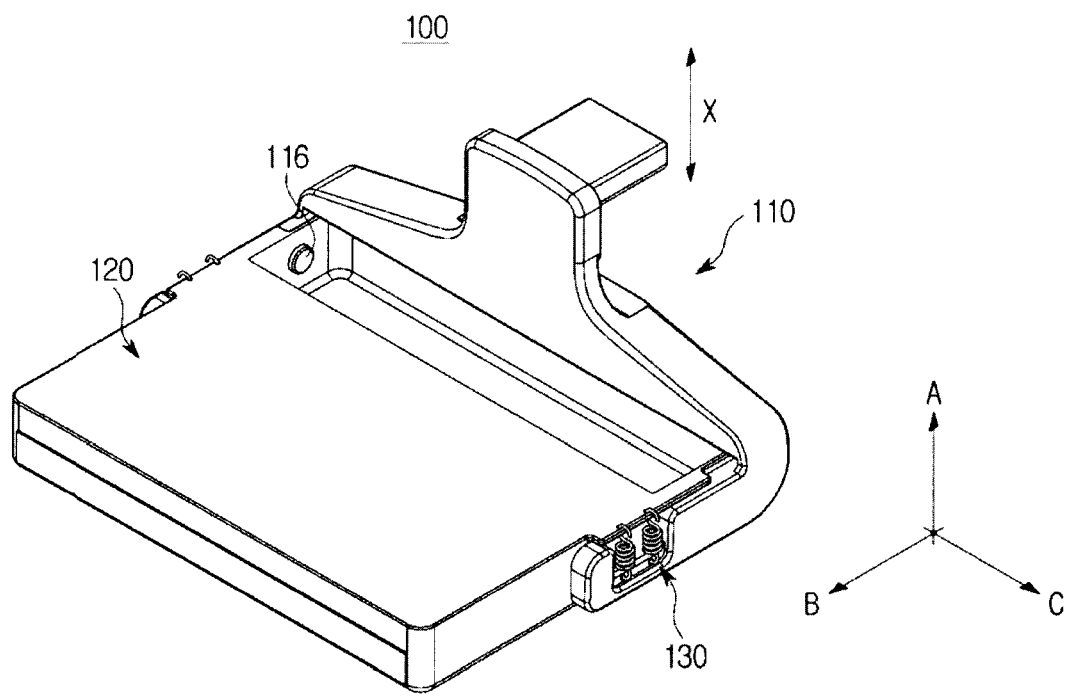
FIG. 6 is a perspective view illustrating a paddle in accordance with a first embodiment in an X-ray imaging apparatus in accordance with an embodiment of the present disclosure.
Figure 7:
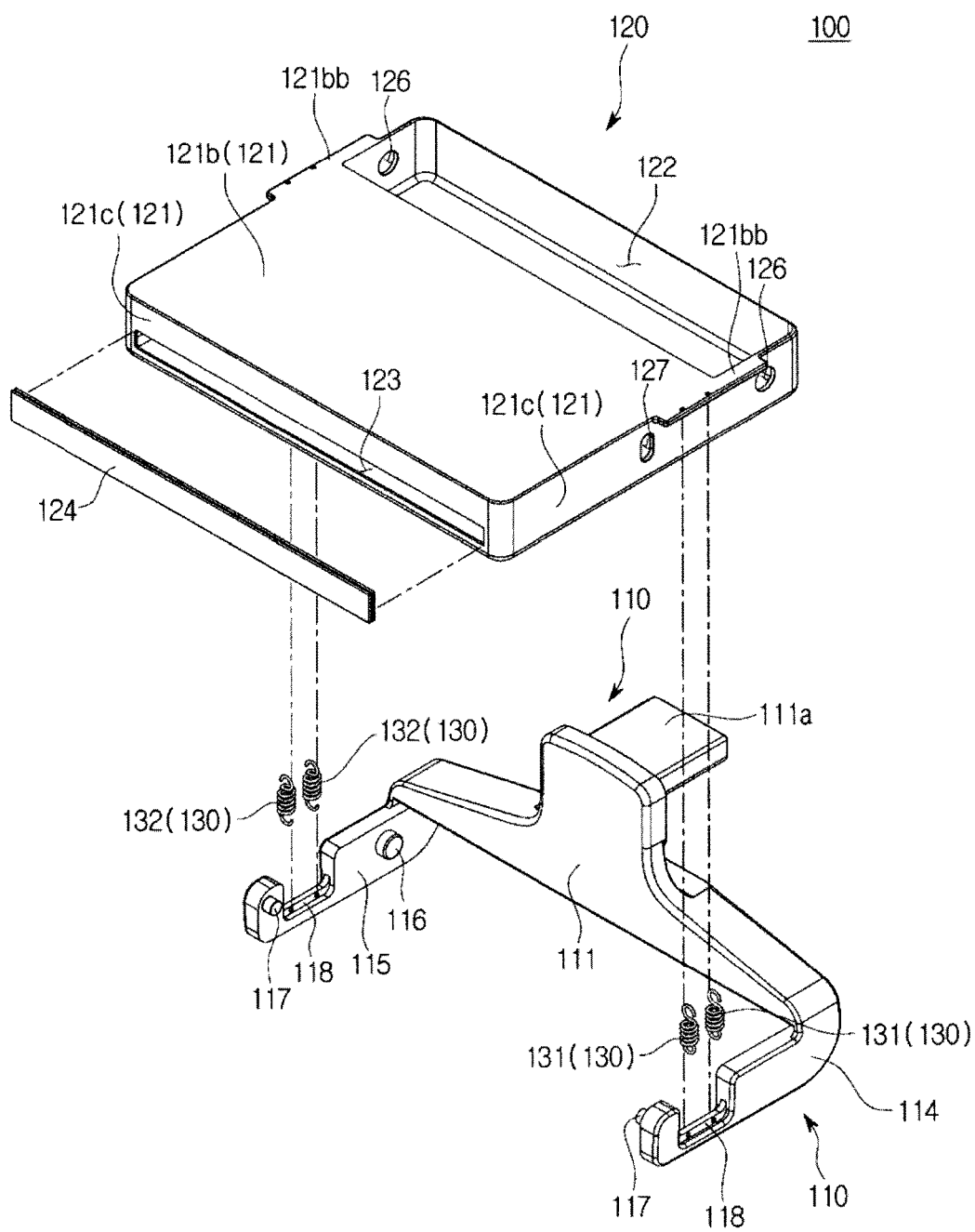
FIG. 7 is an exploded-perspective view illustrating a paddle of FIG. 6 in accordance with the first embodiment of the present disclosure.

FIG. 6 is a perspective view illustrating a paddle in accordance with a first embodiment in an X-ray imaging apparatus in accordance with an embodiment of the present disclosure and FIG. 7 is an exploded-perspective view illustrating a paddle of FIG. 6 in accordance with the first embodiment of the present disclosure. Hereinafter the numeral reference not shown may refer to FIG. 1. Hereinafter a direction toward an object may be defined as a front side of the paddle 100, and a direction toward the frame 11 may be defined as a rear side of the paddle 100.

As illustrated in FIGS. 6 and 7, the paddle 100 may be arranged to be vertically adjustable between the X-ray source 20 and the X-ray detector 41 to compress an object placed on the object contact unit 42 of the X-ray detector 41. Particularly, the paddle 100 may be arranged so as to be raised or lowered between the X-ray source 20 and the X-ray detector 41 along the frame 11 to compress the object placed on the object contact unit 42 of the X-ray detector 41. The paddle 100 may be detachably coupled to the frame 11.

The paddle 100 may include a supporting member 110.

The supporting member 110 may include a body 111. The body 111 may include a coupling unit 111a configured to be detachably coupled to the frame 11. Particularly, the coupling unit 111a may be detachably coupled to a coupling groove (not shown) formed in the frame 11. The coupling unit 111a may be expanded toward the rear side of the paddle 100 from the body 111.

The supporting member 110 may further include a plurality of arms 114 and 115. The plurality of arms 114 and 115 may be formed integrally with the body 111. Or the plurality of arms 114 and 115 may be coupled to the body 111 through a fixing member (not shown). The plurality of arms 114 and 115 may include a first arm 114 toward the right side of the paddle 100, and a second arm 115 toward the left side of the paddle.

A pressure member 120 may be disposed inward of the supporting member 110. Particularly, the body 111 of the supporting member 110 may be disposed on the rear side of the pressure member 120. The plurality of arms 114 and 115 of the supporting member 110 may be disposed respectively on the lateral sides of the pressure member 120 to face opposite sides of the pressure member 120. The first arm 114 may be disposed to face the right side of the pressure member 120, and the second arm 115 may be disposed to face the left side of the pressure member 120.

With continued reference to FIG. 7, the supporting member 110 may further include a rotary shaft 116. Particularly, the rotary shaft 116 may be formed in the plurality of arms 114 and 115 to be protruded toward the inside of the paddle 100 so that the pressure member 120 may be coupled to the rotary shaft 116 to be rotatably moved. On the opposite sides of the pressure member 120, a shaft hole 126 to which the rotary shaft 116 is passed through and coupled may be formed. The rotary shaft 116 may form a rotating axis, which is coupled to the shaft hole 126 so that the pressure member 120 may perform a rotary motion.

The supporting member 110 may further include an interference protrusion 117. Particularly, the interference protrusion 117 may be formed in the plurality of arms 114 and 115 so as to protrude inward toward the inside of the paddle 100. The interference protrusion 117 may be provided in the plurality of arms 114 and 115 in parallel with the rotary shaft 116. On the opposite sides of the pressure member 120, an interference hole 127 may be formed. Particularly, the interference hole 117 may be formed on the opposite sides of the pressure member 120 facing the plurality of arms 114 and 115. The interference hole 127 may be formed to along in an elevation direction (X) of the paddle 100. The interference protrusion 117 may be inserted into the interference hole 127 so that the rotation of the pressure member 120 may be limited. When an external force is not applied to the pressure member 120, the interference protrusion 117 may be disposed on a first position of the interference hole 127 which is toward an upper side in the elevation direction (X) of the paddle 100. When an external force is applied to the pressure member 120, in other words, when the pressure member 120 compress the object, the interference protrusion 117 may be disposed on a second position of the interference hole 127 which is toward a lower side in the elevation direction (X) of the paddle 100.

The supporting member 110 may further include an adjustment member installation unit 118 in which at least one adjustment member 130, 230, 330, and 430 is installed. The adjustment member installation unit 118 may be formed to be recessed in the plurality of arms 114 and 115 in the elevation direction (X) of the paddle 100. The adjustment member installation unit 118 may be provided between the rotary shaft 116 and the interference protrusion 117. One end portion of the at least one adjustment member 130, 230, 330, and 430 may be fixedly coupled to the adjustment member installation unit 118.

The paddle 100 may further include the pressure member 120. The pressure member 120 may be coupled to the supporting member 110 to compress the object. In addition, the pressure member 120 may be rotatably coupled to the supporting member 110 via a hinge.

The pressure member 120 may include a case 121 forming an exterior thereof and having an inner space. The case 121 may have a box shape to supplement the strength of the pressure member 120. However, the shape of the case 121 is not limited to the box shape, and may be modified in various shapes.

The case 121 may include an object compression surface 121a compressing an object, a corresponding surface 121b facing the object compression surface 121a, and a plurality of connection surface 121c connecting the object compression surface 121a (FIG. 8B) to the corresponding surface 121b. The object compression surface 121a may face the object contact unit 42 included in the X-ray detector 41. Particularly, the object may be compressed between the object compression surface 121a and the object contact unit 42 of the X-ray detector 41. The object compression surface 121a may be toward a lower side in the elevation direction (X) of the paddle 100, and the corresponding surface 121b may be toward an upper side in the elevation direction (X) of the paddle 100. The plurality of connection surfaces 121c may include both lateral sides of the case 121, a front surface toward the front side of the paddle 100, and a rear surface toward the rear side of the paddle 100.

The pressure member 120 may further include an opening unit 122. The opening unit 122 may be formed on at least one of the corresponding surface 121b and the plurality of connection surface 121c to be communicated with the inner space of the pressure member 120. Particularly, the opening unit 122 may be formed on a portion of the corresponding surface 121b to be communicated with the inner space of the pressure member 120. Through the opening unit 122, the inner space of the case 121 may be kept in clean. That is, the inner space of the case 121 may be washed through the opening unit 122, and thus foreign materials stacked on the inner space of the case 121 may be effectively removed. The foreign materials stacked on the inner space of the case 121 may interrupt an X-ray imaging and thus it may be very important to remove the foreign material.

The pressure member 120 may further include a slit 123 formed therein. The pressure member 120 may be elastically deformed when an external force is applied. The elastic deformation of the pressure member 120 may be implemented by the slit 123. The slit 123 may be formed along at least one side of the pressure member 120 so that the pressure member 120 may be elastically deformed when an external force is applied to the pressure member 120, i.e. when the pressure member 120 compresses the object. Particularly, the slit 123 may be formed on a front surface of the case 121 toward the front side of the paddle 100.

The elastic deformation of the pressure member 120 may be realized through the slit 123, but during the X-ray procedure, it may frequently occur that a part of the object is caught in the slit 123. To prevent those cases, the pressure member 120 may further include a slit cover 124. The slit cover 124 may be detachably coupled to the slit 123, and may include elastic material. The slit cover 124 may include at least one of a plastic, a rubber, silicon, or another elastomeric material.

The paddle 100 may further include at least one adjustment member 130, 230, 330 and 430. The at least one adjustment member 130, 230, 330 and 430 may be disposed between the supporting member 110 and the pressure member 120 so that the movement of the pressure member 120 may be regulated according to the shape of the object when the pressure member 120 compresses the object. Particularly, the at least one adjustment member 130, 230, 330 and 430 may be disposed between the supporting member 110 and the pressure member 120 so that the movement of the pressure member 120 may be regulated according to the size of the external force applied to the pressure member 120 when the external force is applied to the pressure member 120.

The at least one adjustment member 130, 230, 330 and 430 may regulate the movement of the pressure member 120 by the elastic force. In this case, the at least one adjustment member 130, 230, 330 and 430 may represent at least one elastic member configured to regulate the movement of the pressure member 120 by the elastic force to compress an object evenly when the pressure member 120 compresses the object.

The at least one adjustment member 130, 230, 330 and 430 may include at least one of a spring, rubber, and silicon. A spring may be used as material of the at least one adjustment member 130, 230, and 330 in the paddle 100 according to a first embodiment, a paddle 200 according to a second embodiment, and a paddle 300 according to a third embodiment, and a rubber or other elastomeric material may be used as material of the at least one adjustment member 430 in a paddle 400 according to a fourth embodiment. The material of the at least one adjustment member 130, 230, 330 and 430 is not limited thereto, and thus any kind of material having the elastic force may be used as the material of the at least one adjustment member 130, 230, 330 and 430.

The pressure member 120 may perform at least one motion of yawing motion, rolling motion, and pitching motion and a description thereof will be described later. The at least one adjustment member 130, 230, 330 and 430 may connect the pressure member 120 to the supporting member 110 so that the pressure member 120 may perform at least one motion of yawing motion, rolling motion, and pitching motion.

With reference to FIG. 7, the at least one adjustment member 130, 230, 330 and 430 may include a first elastic member 130. The first elastic member 130 may be disposed on a lateral side of the pressure member 120 to connect the pressure member 120 to the supporting member 110. In other words, the first elastic member 130 may connect the pressure member 120 and the supporting member 110 to be tensioned in a rotary direction of the pressure member 120. Particularly, the first elastic member 130 may be coupled to an extension unit 121*bb* extended toward an outside of the paddle 100 from the corresponding surface 121*b* while being coupled to the adjustment member installation unit 118 formed in the plurality of arms 114 and 115. That is, an end portion of the first elastic member 130 may be fixedly coupled to the adjustment member installation unit 118 and another end portion of the first elastic member 130 may be fixedly coupled to the extension unit 121*bb* of the corresponding surface 121*b*.

The first elastic member 130 may include a first elastic unit 131 and a second elastic unit 132. The first elastic unit 131 may be installed on a lateral side of the pressure member 120. For example, the first elastic unit 131 may be installed on a right side of the pressure member 120. The second elastic unit 132 may be installed on another side of the pressure member 120 to correspond to the first elastic unit 131. For example, the second elastic unit 132 may be installed on a left side of the pressure member 120. The first elastic unit 131 and the second elastic unit 132 may be disposed to face to be symmetrical with respect to the pressure member 120. The first elastic unit 131 and the second elastic unit 132 may be individually extendable so that the pressure member 120 may evenly apply a compression force to the object based on the shape of the object. For example, when the first elastic unit 131 is adjacent to a part of an object, which has more volume, the first elastic unit 131 may be more extended than the second elastic unit 132 in the rotary direction of the pressure member 120.

Hereinafter an operation state of the paddle 100 will be described.

Figure 8A:
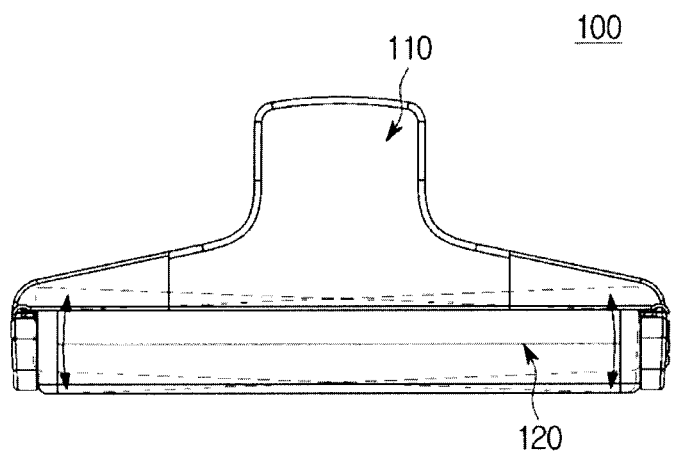
FIG. 8A and FIG. 8B are views illustrating an operation state of a paddle of FIG. 6 in accordance with the first embodiment of the present disclosure.
Figure 8B:
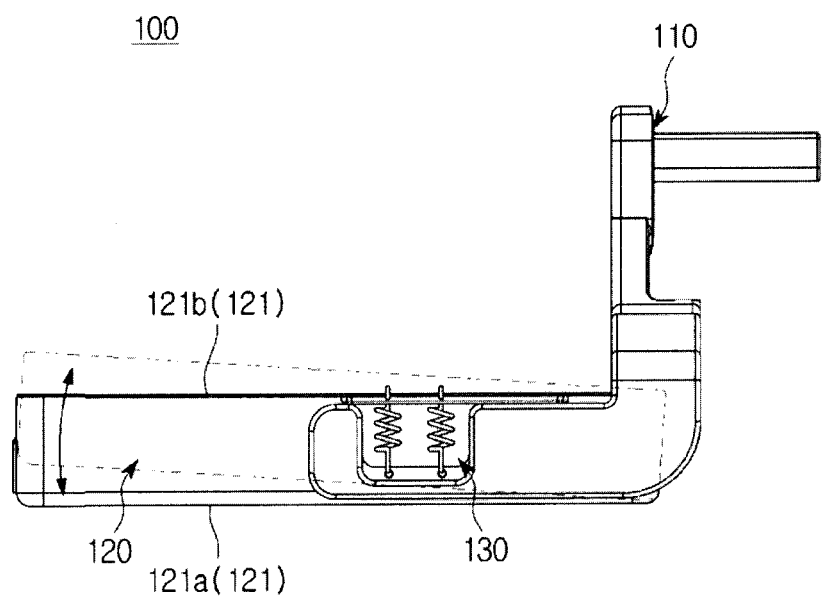

FIGS. 8A and 8B are views illustrating an operating state of a paddle of FIG. 6 in accordance with the first embodiment. Hereinafter the numeral reference may be shown in FIGS. 1, 6, and 7.

As illustrated in FIGS. 8A and 8B, the paddle 100 may be deformable in three dimensions to evenly apply a compression force or pressure force to an object having an unbalanced shape. Particularly, the pressure member 120 may perform at least one motion of yawing motion of rotating with respect to a first axis (A) in parallel with the elevation direction (X) of the paddle 100, rolling motion of rotating with respect to a second axis (B) perpendicular to the first axis (A) to be toward the object, and pitching motion of rotating with respect to a third axis (C) perpendicular to the first axis (A) and the second axis (B).

The paddle 100 according to the first embodiment may perform at least one of the rolling motion and the pitching motion. FIG. 8A illustrates a rolling motion of the pressure member 120 of the paddle 100 in accordance with the first embodiment. FIG. 8B illustrates a pitching motion of the pressure member 120 of the paddle 100 in accordance with the first embodiment.

The pressure member 120 may compress or press the object 500 placed between the object contact unit 42 and the object compression surface 121*a* by a restoring force of the first elastic member 130, which is tensioned in the rotary direction of the pressure member 120.

Figure 9:
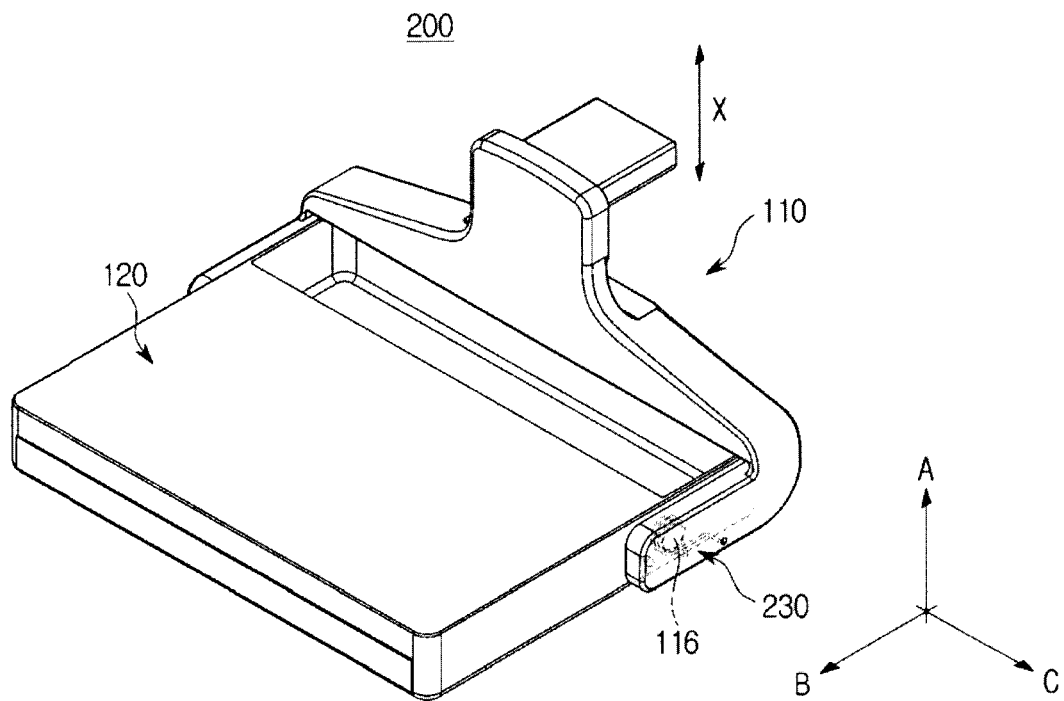
FIG. 9 is a perspective view illustrating a paddle in accordance with a second embodiment in an X-ray imaging apparatus in accordance with an embodiment of the present disclosure.
Figure 10:
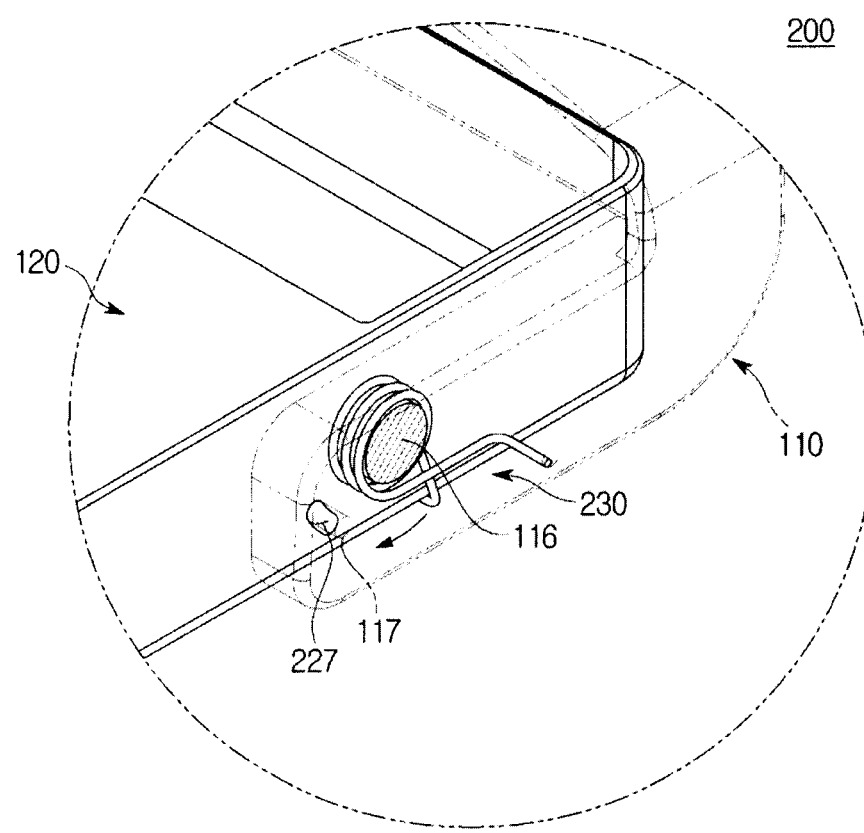
FIG. 10 is an enlarged-perspective view illustrating a part of the paddle of FIG. 9 in accordance with the second embodiment of the present disclosure.
Figure 11:
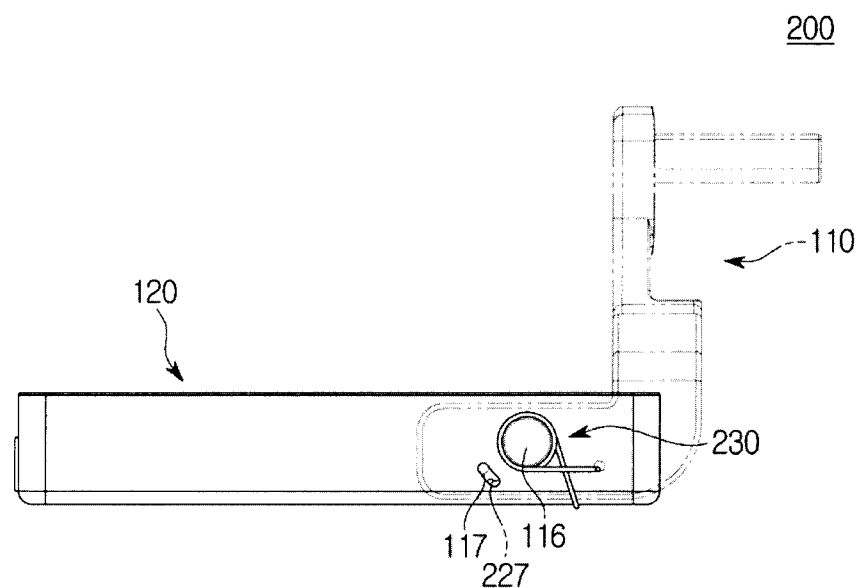
FIG. 11 is a lateral view illustrating the paddle of FIG. 9 in accordance with the second embodiment of the present disclosure.

FIG. 9 is a perspective view illustrating a paddle in accordance with a second embodiment in an X-ray imaging apparatus in accordance with an embodiment of the present disclosure, FIG. 10 is an enlarged-perspective view illustrating a part of the paddle of FIG. 9 in accordance with the second embodiment and FIG. 11 is a lateral view illustrating the paddle of FIG. 9 in accordance with the second embodiment. Hereinafter a description of the same part as the paddle 100 according to the first embodiment will be omitted.

As illustrated in FIGS. 9, 10 and 11, the at least one adjustment member 130, 230, 330 and 430 may include a second elastic member 230. The second elastic member 230 may wind around the rotary shaft 116. Particularly, the second elastic member 230 may wind around a part of the rotary shaft 116 placed between the plurality of arms 114 and 115, and the pressure member 120. One end portion of the second elastic member 230 may be fixedly coupled to the plurality of arms 114 and 115, and another end portion of the second elastic member 230 may be fixedly coupled to the pressure member 120. The second elastic member 230 may include a torsion spring.

The supporting member 110 may include an interference protrusion 117 that is formed in the plurality of arms 114 and 115 to protrude toward the inner side of the paddle 200. The interference protrusion 117 may be provided in the plurality of arms 114 and 115 in parallel with the rotary shaft 116.

On the opposite sides of the pressure member 120 facing the plurality of arms 114 and 115, an interference hole 227 may be formed. The interference protrusion 117 may be inserted into the interference hole 227 so that the rotation of the pressure member 120 may be limited. The interference hole 227 may be formed to be long to be inclined toward the front side of the paddle 200 in the elevation direction (X) of the paddle 200. When an external force is not applied to the pressure member 120, the interference protrusion 117 may be disposed on a first position of the interference hole 227, which is toward an upper side in the elevation direction (X) of the paddle 200 while toward a front side of the paddle 200. When an external force is applied to the pressure member 120 that is the pressure member 120 compresses the object, the interference protrusion 117 may be disposed on a second position of the interference hole 227, which is toward a lower side in the elevation direction (X) of the paddle 100 while toward a rear side of the paddle 200.

The paddle 200 according to the second embodiment may perform at least one of rolling motion and pitching motion.

Figure 12:
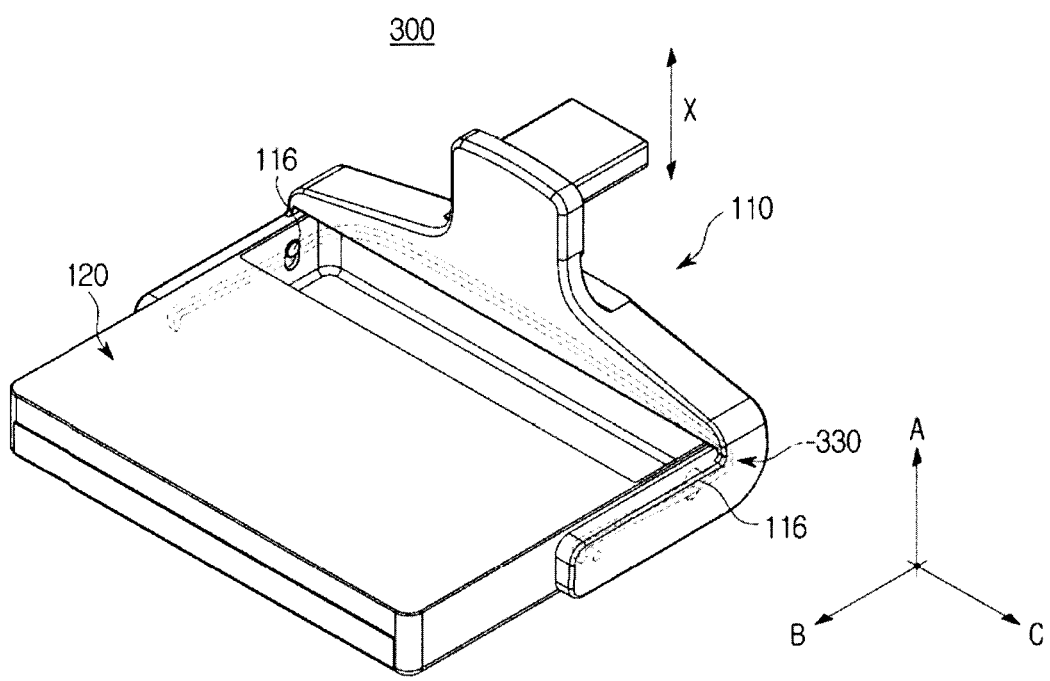
FIG. 12 is a perspective view illustrating a paddle in accordance with a third embodiment in an X-ray imaging apparatus in accordance with an embodiment of the present disclosure.
Figure 13:
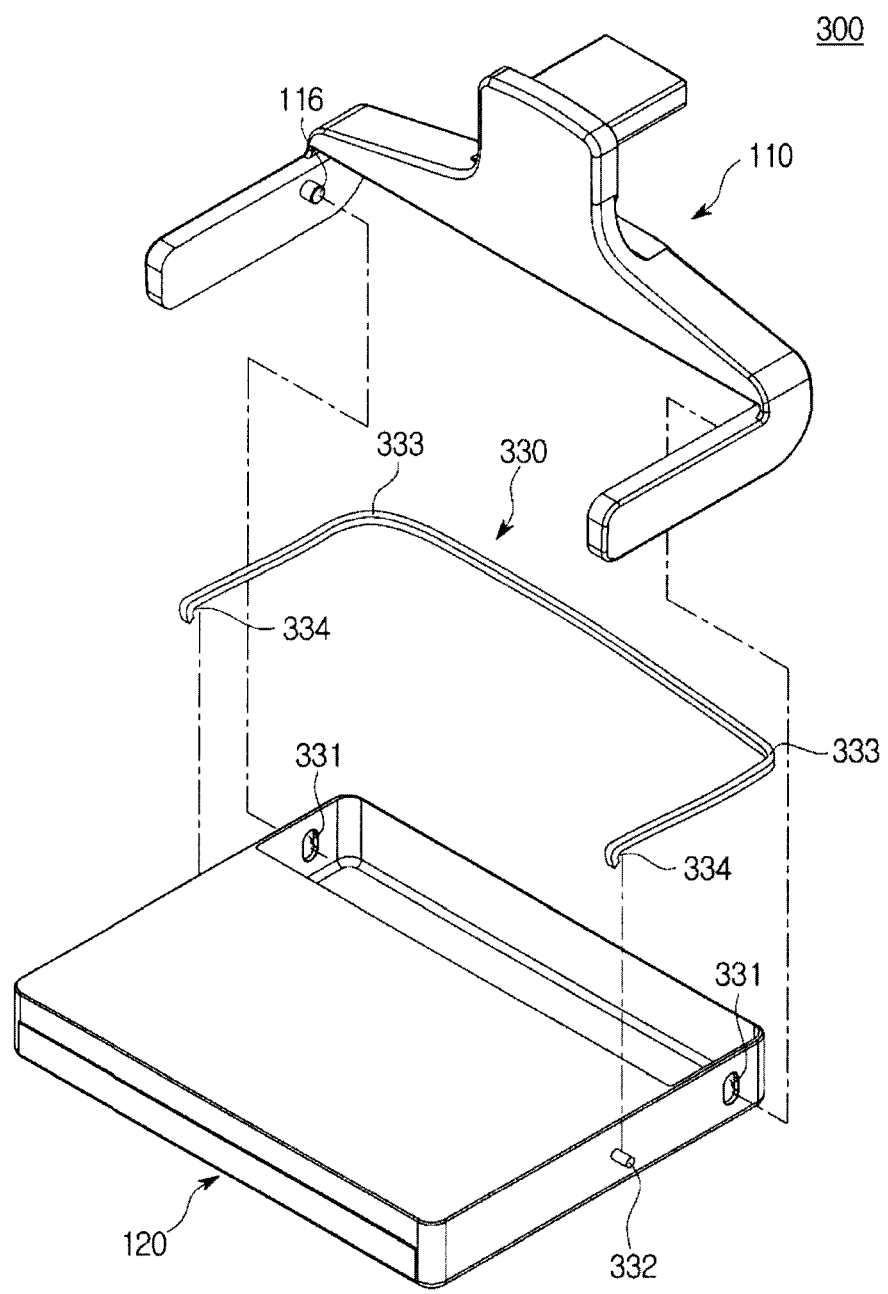
FIG. 13 is an exploded-perspective view illustrating the paddle of FIG. 12 in accordance with the third embodiment of the present disclosure.
Figure 14:
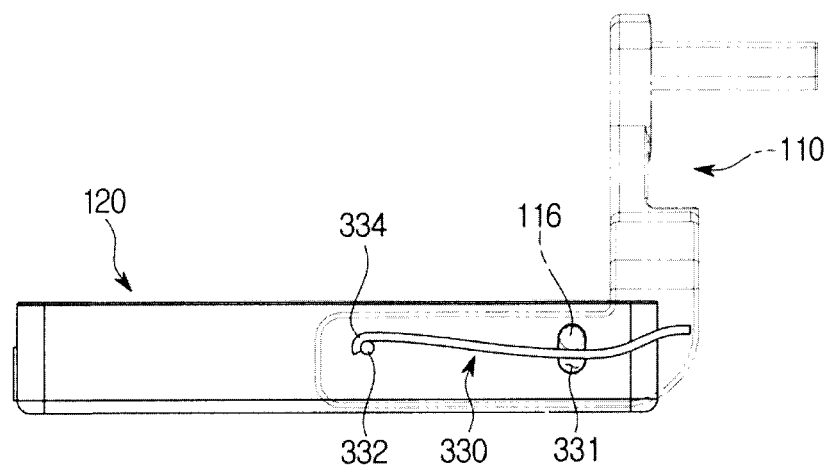
FIG. 14 is a lateral view illustrating the paddle of FIG. 12 in accordance with the third embodiment of the present disclosure.

FIG. 12 is a perspective view illustrating a paddle in accordance with a third embodiment in an X-ray imaging apparatus in accordance with an embodiment of the present disclosure, FIG. 13 is an exploded-perspective view illustrating the paddle of FIG. 12 in accordance with the third embodiment and FIG. 14 is a lateral view illustrating the paddle of FIG. 12 in accordance with the third embodiment. Hereinafter a description of the same part as the paddle 100 according to the first embodiment will be omitted.

As illustrated in FIGS. 12 to 14, the at least one adjustment member 130, 230, 330 and 430 may include a third elastic member 330.

The pressure member 120 may include a shaft coupling hole 331. The shaft coupling hole 331 may be formed to be long in the elevation direction (X) of the paddle 300 so that the rotary shaft 116 may be moved while being inserted into the opposite sides of the pressure member 120 facing the plurality of arms 114 and 115.

The pressure member 120 may further include a fixing protrusion 332. The fixing protrusion 332 may be provided on the both lateral sides of the pressure member 120 to protrude outward of the pressure member 120. The fixing protrusion 332 may be provided parallel with the rotary shaft 116.

The third elastic member 330 may include a wire spring. Particularly, the third elastic member 330 may be a wire spring configured to be expanded along the both lateral sides and the rear side of the pressure member 120. The third elastic member 330 may be a wire spring including at least one bending unit 333. FIGS. 12 and 13 illustrate a wire spring including two bending units 333 as an example of the third elastic member 330.

Opposite ends of the third elastic member 330 may be coupled to the fixing protrusion 332 in a locking manner. Particularly, a hook unit 334 may be formed in the opposite ends of the third elastic member 330 and the hook unit 334 may be coupled to the fixing protrusion 332 in a locking manner.

The third elastic member 330 may be disposed on a lower side of the rotary shaft 116 in the elevation direction (X) of the paddle 300 to support the rotary shaft 116. Particularly, the third elastic member 330 may be disposed along both lateral sides and a rear side of the pressure member 120 to be placed in the lower side of the rotary 116 in the elevation direction (X) of the paddle 300. Both end portions of the third elastic member 330 may be coupled to the fixing protrusion 332 in a locking manner.

When an external force is not applied to the pressure member 120, the third elastic member 330 may support the rotary shaft 116 so that the rotary shaft 116 may be placed in a first position of the shaft coupling hole 331 placed in an upper side in the elevation direction (X) of the paddle 300. When an external force is applied to the pressure member 120, in other words, when the pressure member 120 compresses the object, the rotary shaft 116 may compress the third elastic member 330 and then moved to a second position of the shaft coupling hole 331 placed in a lower side in the elevation direction (X) of the paddle 300.

The paddle 300 according to the third embodiment may perform at least one of rolling motion and pitching motion.

Figure 15:
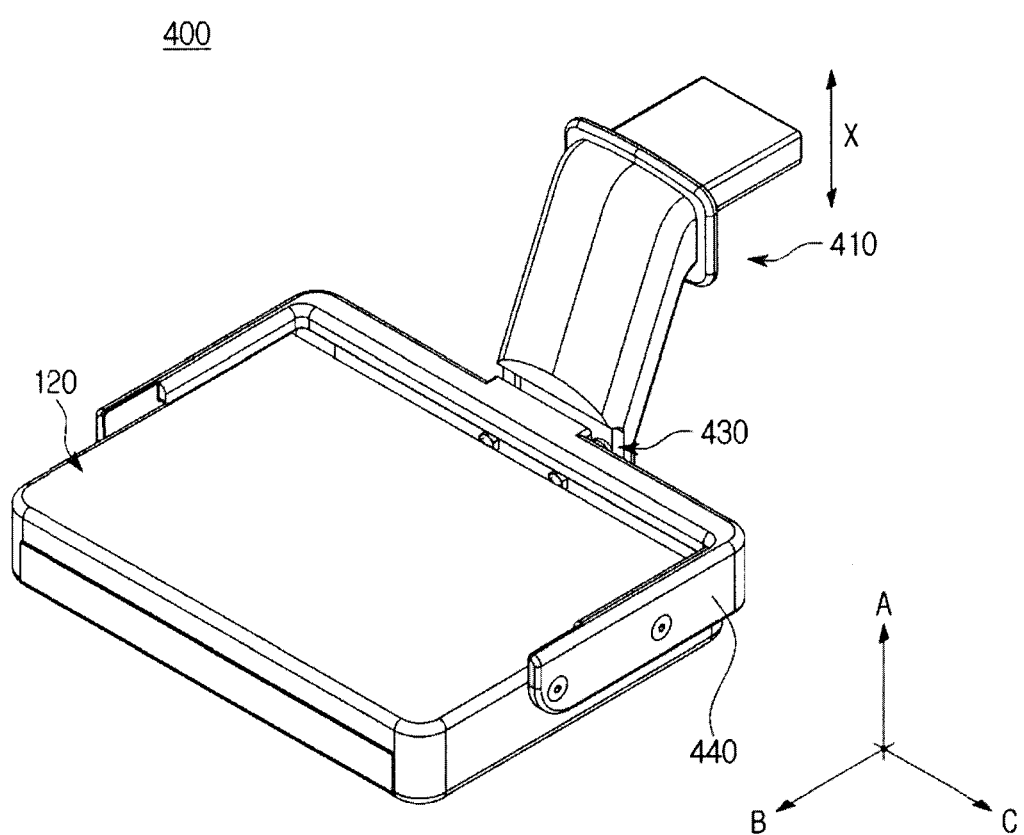
FIG. 15 is a perspective view illustrating a paddle in accordance with a fourth embodiment in an X-ray imaging apparatus in accordance with an embodiment of the present disclosure.
Figure 16:
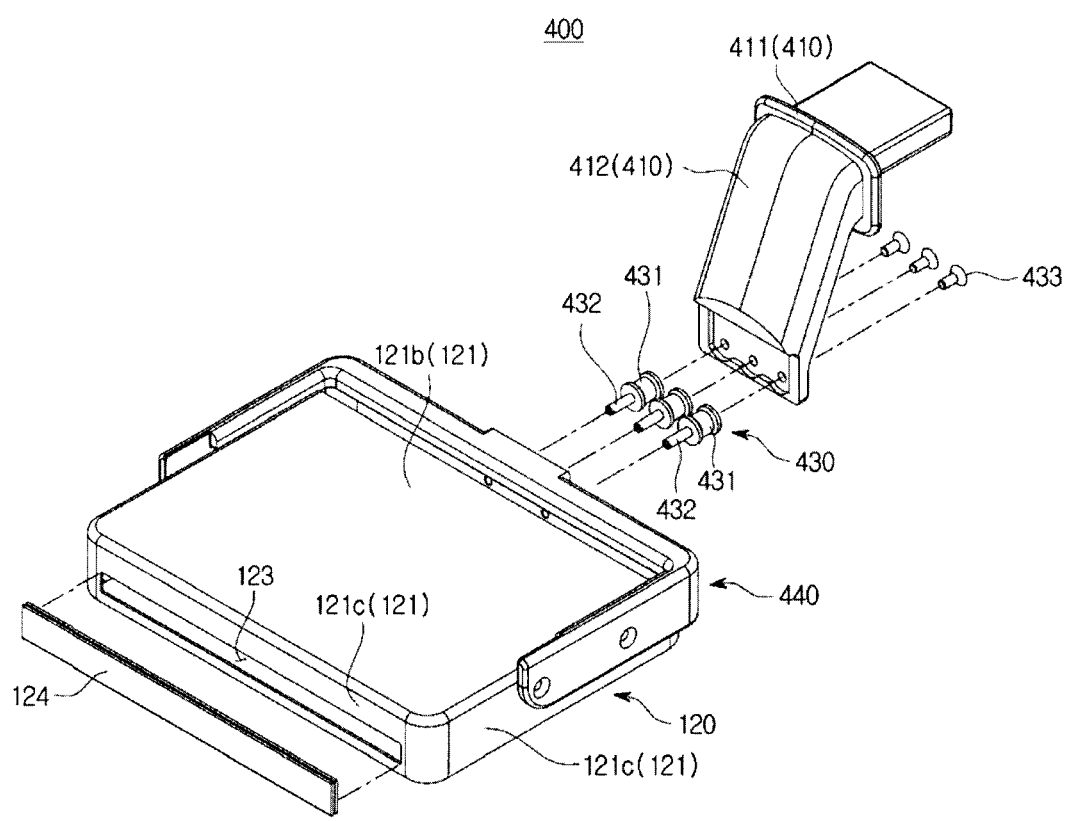
FIG. 16 is an exploded-perspective view illustrating the paddle of FIG. 15 in accordance with the fourth embodiment of the present disclosure.
Figure 17A:
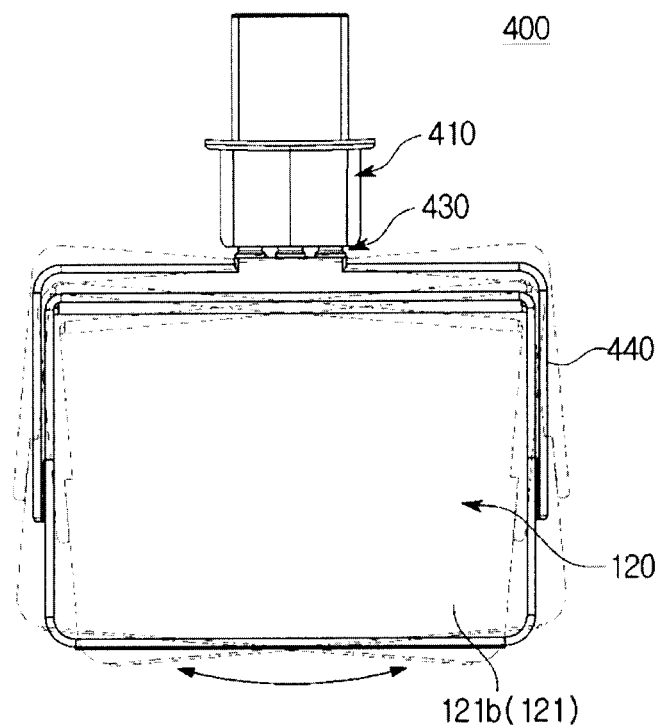
FIG. 17A, FIG. 17B and FIG. 17C are views illustrating an operation state of a paddle of FIG. 15 in accordance with the fourth embodiment of the present disclosure.
Figure 17B:
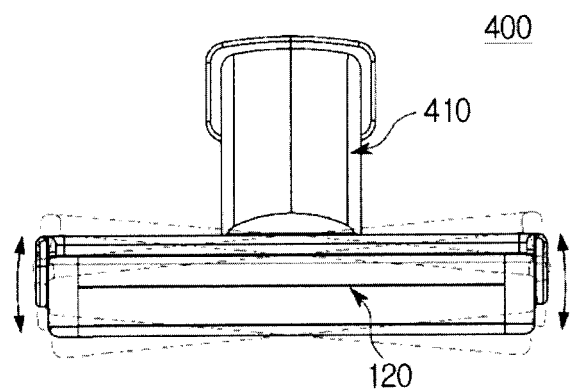
Figure 17C:
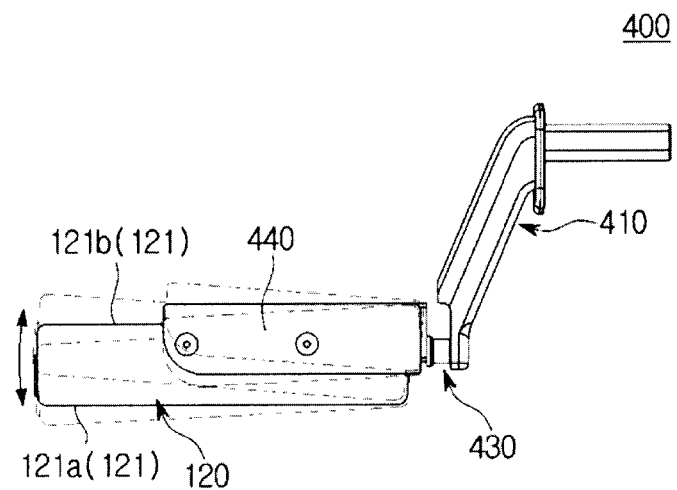

FIG. 15 is a perspective view illustrating a paddle in accordance with a fourth embodiment in an X-ray imaging apparatus in accordance with an embodiment of the present disclosure, FIG. 16 is an exploded-perspective view illustrating the paddle of FIG. 15 in accordance with the fourth embodiment and FIGS. 17A and 17C are views illustrating an operation state of a paddle of FIG. 15 in accordance with the fourth embodiment. Hereinafter a description of the same part as the paddle 100 according to the first embodiment will be omitted. In FIG. 16, a first fixing member 432 may be coupled to a first coupling unit.

As illustrated in FIGS. 15 and 16, a paddle 400 may include a supporting member 410.

As shown in FIG. 16, the supporting member 410 may include a first supporting member 411 and a second supporting member 412.

The first supporting member 411 may be detachably coupled to a coupling groove (not shown) formed in the frame 11. The first supporting member 411 may be coupled to the second supporting member 412 to be toward a rear side of the paddle 400. Particularly, the first supporting member 411 may be coupled to the second supporting member 412 through a fixing member (not shown). Or the first supporting member 411 and the second supporting member 412 may be formed integrally each other.

The second supporting member 412 may be disposed on a rear side of the pressure member 120. In addition, the second supporting member 412 may be coupled to the pressure member 120. Particularly, the second supporting member 412 may be coupled to an installation frame 440 of the pressure member 120. The second supporting member 412 may face the pressure member 120 with respect to at least one adjustment member 430. Particularly, the second supporting member 412 may face the installation frame 440 with respect to the at least one adjustment member 430. The at least one adjustment member 430 may connect the installation frame 440 of the pressure member 120 to second supporting member 412 of the supporting member 410, and a description thereof will be described later.

The paddle 400 may further include a pressure member 120. The pressure member 120 may be coupled to the supporting member 410 to compress an object. The pressure member 120 may be disposed on a front side of the supporting member 410. Particularly, the pressure member 120 may be coupled to the front side of the supporting member 410.

The pressure member 120 may include a case 121 forming an exterior thereof and having an inner space. The case 121 may have a box shape to supplement the strength of the pressure member 120. However, the shape of the case 121 is not limited to the box shape, and may be modified in various shapes.

The case 121 may include an object compression surface 121a compressing an object, a corresponding surface 121b facing the object compression surface 121a, and a plurality of connection surface 121c connecting the object compression surface 121a to the corresponding surface 121b.

The pressure member 120 may further include an opening unit (not shown). The opening unit may be formed on at least one of the corresponding surface 121b and the plurality of connection surface 121c to be communicated with the inner space of the pressure member 120. Particularly, the opening unit may be formed on a portion of any one of the plurality of connection surface 121c facing the rear side of the paddle 400 to be communicated with the inner space of the pressure member 120. In other words, the opening unit may be formed on a portion of any one of the plurality of connection surface 121c facing the installation frame 440. The inner space of the case 121 may be washed through the opening unit, and thus foreign materials stacked on the inner space of the case 121 may be effectively removed.

The pressure member 120 may further include a slit 123. The elastic deformation of the pressure member 120 may be implemented by the slit 123. The slit 123 may be formed along at least one side of the pressure member 120. Particularly, the slit 123 may be formed on a front surface of the case 121 toward the front side of the paddle 400. The slit 123 may be formed along in a vertical direction of the paddle 400.

The pressure member 120 may further include a slit cover 124. The slit cover 124 may be detachably coupled to the slit 123, and may include elastic material. The slit cover 124 may include at least one of a rubber and silicon.

The pressure member 120 may further include the installation frame 440. The installation frame 440 may be coupled to an outside of the pressure member 120. Particularly, the installation frame 440 may be coupled to the outside of the pressure member 120 to cover a portion of the plurality of connection surface 121c of the case 121. Particularly, the installation frame 440 may be coupled to the outside of the pressure member 120 to cover a right side toward the right side of the paddle 400, a left side toward the left side of the paddle 400, and a rear side toward the rear side of the paddle 400 among the plurality of connection surface 121c of the case 121. On the other side, the installation frame 440 may be coupled to a single side of the pressure member 120 facing the supporting member 410 to be moved together with the pressure member 120. The installation frame 440 may be fixedly coupled to the pressure member 120 by a coupling member (not shown) to be moved together with the pressure member 120. Particularly, the installation frame 440 may be fixedly coupled to both sides of the pressure member 120 through the coupling member.

The paddle 400 may further include at least one adjustment member 430. When a direction toward the object 500 is referred to as a front side of the paddle 400 or a front side of the pressure member 120, the at least one adjustment member 430 may be disposed in a rear side of the pressure member 120 to connect the pressure member 120 to the supporting member 410. Particularly, the at least one adjustment member 430 may be disposed between the installation frame 440 and the supporting member 410 to connect the installation frame 440 of the pressure member 120 to the second supporting member 412 of the supporting member 410.

The at least one adjustment member 430 may regulate the movement of the pressure member 120 by an elastic force.

The at least one adjustment member 430 may include at least one of spring, rubber and silicon. In the paddle 400 according to the fourth embodiment, the at least one adjustment member 430 may be formed of rubber or another elastomeric material. The rubber may be synthetic or natural. Particularly, a soft part 431 of the at least one adjustment member 430 may be formed of rubber. The material of the at least one adjustment member 430 is not limited thereto, and thus any material having the elastic force may be used as the at least one adjustment member 430.

The pressure member 120 may perform at least one motion of yawing motion, rolling motion, and pitching motion and a description thereof will be described. The at least one adjustment member 430 may connect the pressure member 120 to the supporting member 410 so that the pressure member 120 may perform at least one motion of yawing motion, rolling motion, and pitching motion.

The at least one adjustment member 430 may include the soft part 431, a first coupling unit, and a second coupling unit. The first coupling unit may be formed in the soft part 431 to face the pressure member 120. Particularly, the first coupling unit may be formed in the soft part 431 to face the installation frame 440. The second coupling unit may be formed in the soft part 431 to face the supporting member 410. Particularly, the second coupling unit may be formed in the soft part 431 to face the second supporting member 412.

The first fixing member 432 that is penetrably coupled to the installation frame 440 may be coupled to the first coupling unit, and the second fixing member 433 that is penetrably coupled to the supporting member 410, particularly the second supporting member 412, may be coupled to the second coupling unit. The first fixing member 432 coupled to the first coupling unit and the second fixing member 433 coupled to the second coupling unit may be spaced apart from each other with a certain distance in the soft part 431. Particularly, the first fixing member 432 coupled to the first coupling unit and the second fixing member 433 coupled to the second coupling unit may be spaced apart from each other with a certain distance in forward and backward of the paddle 40 in the soft part 431. Accordingly, the at least one adjustment member 430 that is the soft part 431 may regulate the movement of the pressure member 120 by being bent or twisted.

Hereinafter an operation state of the paddle 400 will be described.

As illustrated in FIGS. 17A to 17C, the paddle 400 may be deformable in three dimensions to evenly apply a compression force or pressure force to an object having an unbalanced shape. Particularly, the pressure member 120 may perform at least one motion of yawing motion of rotating with respect to a first axis (A) in parallel with the elevation direction (X) of the paddle 400, rolling motion of rotating with respect to a second axis (B) perpendicular to the first axis (A) to be toward the object, and pitching motion of rotating with respect to a third axis (C) perpendicular to the first axis (A) and the second axis (B).

The paddle 400 according to the fourth embodiment may perform at least one of the yawing motion, the rolling motion and the pitching motion. FIG. 17A illustrates a yawing motion of the pressure member 120 of the paddle 400 in accordance with the fourth embodiment. FIG. 17B illustrates a rolling motion of the pressure member 120 of the paddle 400 in accordance with the fourth embodiment. FIG. 17C illustrates a pitching motion of the pressure member 120 of the paddle 400 in accordance with the fourth embodiment.

When the pressure member 120 performs the yawing motion, the at least one adjustment member 430 may be moved in the right and left direction of the paddle 400. Particularly, when the pressure member 120 performs the yawing motion, the at least one adjustment member 430 may be bent or twisted in the right and left direction of the paddle 400.

When the pressure member 120 performs the pitching motion, the at least one adjustment member 430 may be moved in the elevation direction (X) of the paddle 400. Particularly, when the pressure member 120 performs the pitching motion, the at least one adjustment member 430 may be bent or twisted in the elevation direction (X) of the paddle 400.

When the pressure member 120 performs the rolling motion, the at least one adjustment member 430 may be twisted.

Figure 18:
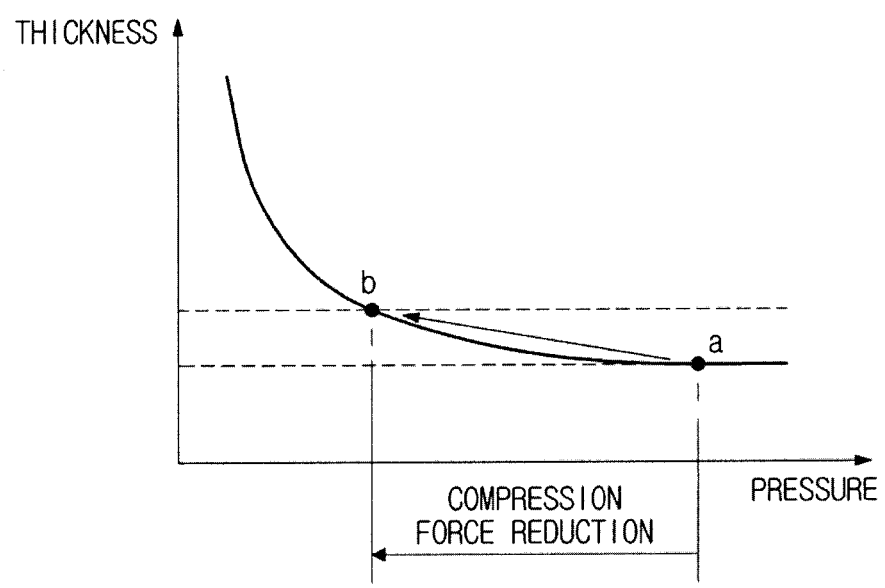
FIG. 18 is a graph illustrating a control method for an X-ray imaging apparatus in accordance with an embodiment of the present disclosure.
Figure 19:
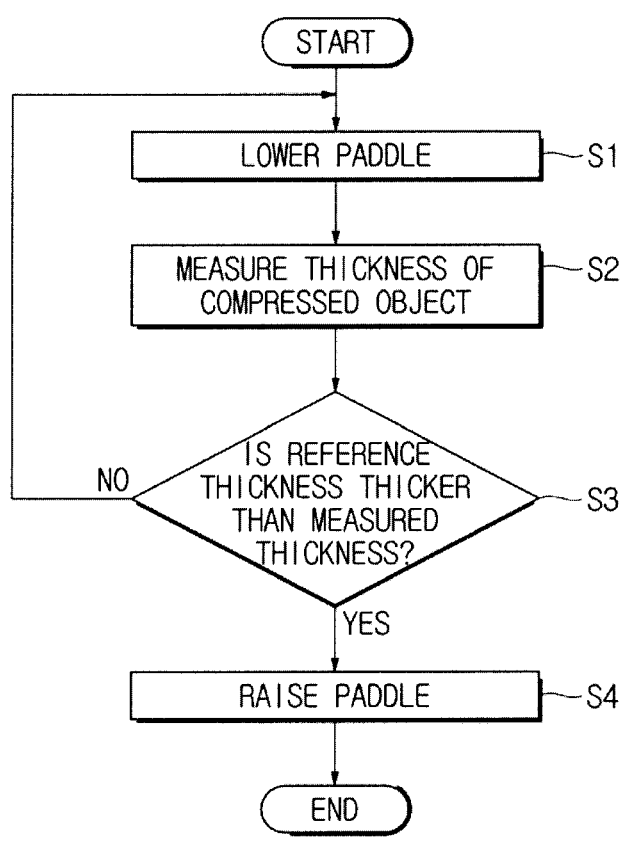
FIG. 19 is a flow chart illustrating a control method for an X-ray imaging apparatus in accordance with an embodiment of the present disclosure.

FIG. 18 is a graph illustrating a control method for an X-ray imaging apparatus in accordance with an embodiment of the present and FIG. 19 is a flow chart illustrating a method for controlling an X-ray imaging apparatus in accordance with an embodiment of the present.

In the process of X-ray imaging, the X-ray imaging apparatus 1 may employ a variety of control methods to prevent a case in which an excessive pressure or compression force is applied to an object in the process of X-ray imaging. This may make it possible to reduce the pain of the patient during the X-ray procedure Hereinafter a variety of control methods of the X-ray imaging apparatus to prevent an excessive pressure or compression force applied to an object will be shown and described.

As illustrated in FIGS. 18 and 19, a control method of the X-ray imaging apparatus may include lowering the paddle 100, 200, 300 and 400 to compress an object (S1), measuring a thickness of the object compressed by the paddle 100, 200, 300 and 400 (S2), comparing the measured thickness of the object with a reference thickness in an imaging condition table (S3), and raising the paddle 100, 200, 300 and 400 to reduce the compression of the object when the reference thickness in the imaging condition table is larger than the thickness of the object (S4).

As mentioned above, since the breast is composed of soft tissues, it may be required to press or compress the breast by using the paddle 100, 200, 300 and 400 to acquire a clear X-ray imaging as much as possible. However, when an excess pressure or compression is applied to the breast, which is over than a certain predetermined level, such pressure or compression may cause the pain or discomfort of the patient but it may rarely effect on the quality of the X-ray imaging. In the embodiment, an imaging condition table may be used to prevent the excessive pressure or compression applied to the object. The imaging condition table may illustrate a variety of condition of imaging related to a range of thickness of the object at the time of completion of the pressure or compression. For example, the imaging condition may include the tube voltage, and the dose of the X-rays (mAs).

Referring now to a graph shown in FIG. 18, the object may be maximally compressed to a first position (a) by lowering the paddle 100, 200, 300 and 400. A thickness of the object that is maximally compressed to the first position (a) may be measured. After measuring the thickness of the object, a range of thickness of the object in the same X-ray irradiation condition may be confirmed by using the imaging condition table. The thickness of the object that is maximally compressed to the first position (a) may be compared with the maximum value in a range of the thickness of the object stored in the imaging condition table, and when the maximum value in the range of the thickness of the object in the imaging condition table is larger than the thickness of the compressed object, the pressure force or the compression force applied to the object 500 may be reduced to a second position (b) by raising the paddle 100, 200, 300 and 400 so as to reduce the amount of compression. In the graph of FIG. 8, the second position (b) may correspond to the maximum value in the range of the thickness of the object under the same X-ray irradiation condition, illustrated in the imaging condition table.

Figure 20:
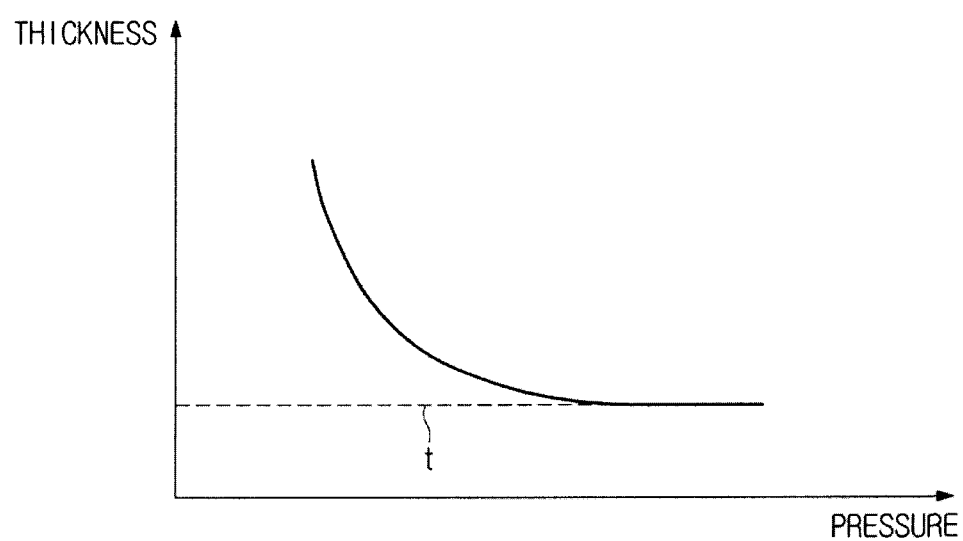
FIG. 20 is a graph illustrating a control method for an X-ray imaging apparatus in accordance with another embodiment of the present disclosure.
Figure 21:
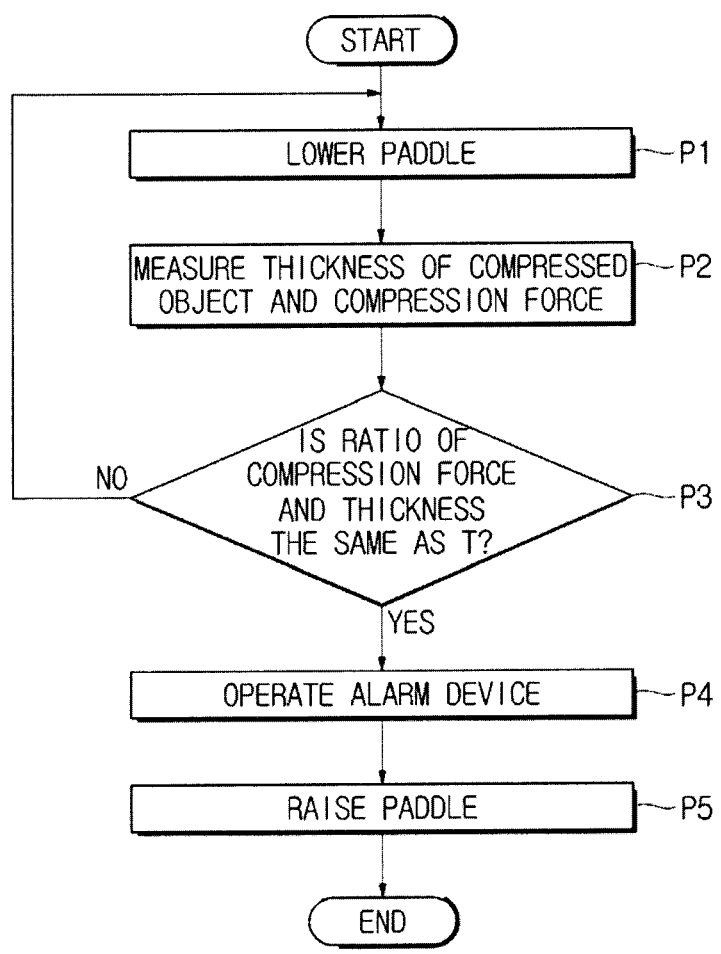
FIG. 21 is a flow chart illustrating a control method for an X-ray imaging apparatus in accordance with another embodiment of the present disclosure.

FIG. 20 is a graph illustrating a control method for an X-ray imaging apparatus in accordance with another embodiment of the present and FIG. 21 is a flow chart illustrating a control method for an X-ray imaging apparatus in accordance with an embodiment of the present.

As illustrated in FIGS. 20 and 21, the X-ray imaging apparatus may be provided with an alarm function configured to provide information related to variation of thickness of an object to a user. The alarm function may be implemented by at least one of visual effect and acoustic effect.

As illustrated in a graph of FIG. 20, the thickness of the object may be inversely proportional to the pressure force or the compression force applied to the object. In other words, as the pressure force or the compression force applied to the object is increased, the thickness of the object may be reduced. However, as illustrated in the graph of FIG. 20, although the pressure force or the compression force above a certain level is applied to the object, the thickness of the object may be no longer reduced. Therefore, in order to reduce the thickness of the object that will be irradiated, it may not be necessary to apply the pressure force or the compression force more than a certain predetermined level. Particularly, in a state in which a ratio of the pressure force or the compression force applied to the object, and a thickness of an object is confirmed, when the ratio reaches a certain value, it may inform the user of stopping the pressure or the compression on the object through the alarm function. Through such an alarm function, it may be possible to prevent the excessive pressure or compression on the object.

As illustrated in FIG. 21, a control method of the X-ray imaging apparatus may include adjusting the position of the paddle, e.g. lowering the paddle 100, 200, 300 and 400 to compress an object (P1), measuring a thickness of the object and the compression force when compressing the object (P2), deriving a ratio of the compression force applied to the object, and the thickness of the object (P3), operating an alarm device when the radio reaches a certain value (t) (P4), and raising the paddle 100, 200, 300 and 400 to compress less the object when the alarm device is operated (P5). At this time, lowering or raising the paddle 100, 200, 300 and 400 may be performed manually by a user.

Figure 22:
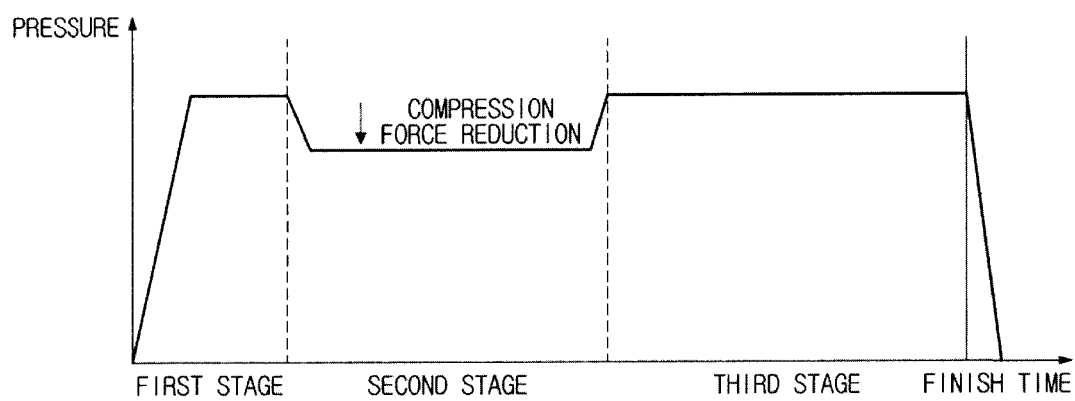
FIG. 22 is a graph illustrating a control method for an X-ray imaging apparatus in accordance with another embodiment of the present disclosure.
Figure 23:
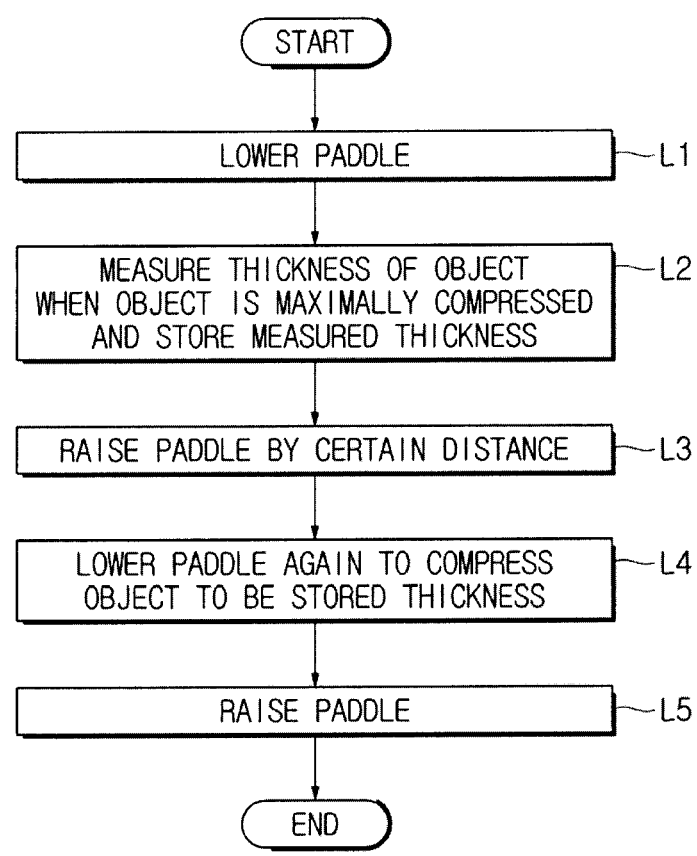
FIG. 23 is a flow chart illustrating a control method for an X-ray imaging apparatus in accordance with another embodiment of the present disclosure.

FIG. 22 is a graph illustrating a control method for an X-ray imaging apparatus in accordance with another embodiment of the present and FIG. 23 is a flow chart illustrating a control method for an X-ray imaging apparatus in accordance with another embodiment of the present.

As illustrated in FIG. 22, the X-ray imaging apparatus may be provided with a function of regulating the pressure force or the compression force, which is applied to the object at each stage.

As illustrated in a graph of FIG. 22, the X-ray imaging may be performed in three stages. In a first stage, a user may maximally press or compress the object of the patient by lowering the paddle 100, 200, 300 and 400. In a no-transitory memory unit (not shown) of the X-ray imaging apparatus, a thickness of the object, which is measured when the object is maximally pressed or compressed, may be stored. In a second stage, the user may operate a workstation. When the user operates the workstation and prepares to irradiate X-rays, the maximum pressure force or the maximum compression force applied to the object of the patient may be reduced by a certain predetermined amount. In other words, the pressure member 120 may be raised from the object by a certain predetermined distance. The reduction of the maximum pressure force or the maximum compression force applied to the object of the patient may be performed as far as the patient's pectoralis major muscle removed from the compression unit. During the preparation of the X-ray irradiation, the pain or discomfort of the patient may be reduced by reducing the maximum pressure force or the maximum compression force applied to the object by a certain amount. In a third stage, X-rays may be emitted to the object. At this time, the paddle 100, 200, 300 and 400 may press the object again by the thickness of the object that is stored the memory unit of the X-ray imaging apparatus. Accordingly, in the third stage, X-rays may irradiate the object while applying the maximum pressure force, or the maximum compression force again, to the object, which was applied to the object in the first stage.

As illustrated in FIG. 23, a control method of the X-ray imaging apparatus may include lowering the paddle 100, 200, 300 and 400 to compress maximally an object (L1), measuring a thickness of the object and storing the measured thickness when maximally pressing or compressing the object (L2), raising the paddle 100, 200, 300 and 400 from the object by a certain distance during the preparation of the X-ray irradiation (L3), lowering the paddle 100, 200, 300 and 400 to press or compress the object again to be a thickness, which is stored, when irradiating the X-rays (L4), and raising the paddle 100, 200, 300 and 400 when the irradiation of the X-ray is completed (L5).

The lowering and raising of the paddle 100, 200, 300 and 400 may be performed by the controller of the X-ray imaging apparatus or by a user in a manual manner. The controller may automatically raise or lower the paddle to conform the pressure to within a range of values, for example, in storage or a table such as discussed herein below.

Hereinbefore, the maximum pressure force or the maximum compression force may represent the pressure force or the compression force at the time the patient complains the pain. In addition, the pressure force or the compression force may be indicated by the pressure.

As is apparent from the above description, according to the proposed X-ray imaging apparatus and the control method thereof, since the object may be compressed by using the pressure member of the paddle configured to perform at least one of yawing motion, rolling motion, and pitching motion, the pain and discomfort that often occurs to a patient's breasts during the X-ray procedure, may be reduced.

By forming a slit in the pressure member, the pressure member may be elastically deformable.

When comparing a reference thickness indicated in the imaging condition table having the same irradiation condition with a real thickness of the object, when the real thickness of the object is thinner than the reference thickness, the excess pressure on the object by the paddle may be prevented by reducing the pressure on the object to a certain predetermined level. It should also be understood and appreciate that the disclosure is not limited to utilizing a table, as these reference values can be stored in other ways as appreciated by a person of ordinary skill in the art.

When the compression of the paddle on the object is performed over a certain predetermined level, a user operating the apparatus may be informed that the patient's breast (or other object) is being excessively compressed, Such notification may occur through an alarm function, sound, lights, voice and thus the excessive pressure on the object by the paddle may be reduced in response to the alarm.

By regulating the compression force of the paddle on the object step by step, the time-duration of the maximum compression force, which is applied to the object, may be reduced.

The apparatuses and methods of the disclosure can be implemented in hardware, and in part as firmware or via the execution of software or computer code in conjunction with hardware that is stored on a non-transitory machine readable medium such as a CD ROM, a RAM, a floppy disk, a hard disk, or a magneto-optical disk, or computer code downloaded over a network originally stored on a remote recording medium or a non-transitory machine readable medium and stored on a local non-transitory recording medium for execution by hardware such as a processor, so that the methods described herein are loaded into hardware such as a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc., that may store or receive software or computer code that when accessed and executed by the computer, processor or hardware implement the processing methods described herein. In addition, it would be recognized that when a general purpose computer accesses code for implementing the processing shown herein, the execution of the code transforms the general purpose computer into a special purpose computer for executing the processing shown herein. In addition, an artisan understands and appreciates that a "processor", "microprocessor" "controller", or "control unit" constitute hardware in the claimed disclosure that contain circuitry that is configured for operation. Under the broadest reasonable interpretation, the appended claims constitute statutory subject matter in compliance with 35 U.S.C. § 101 and none of the elements are software per se. No claim element herein is to be construed under the provisions of 35 U.S.C. 112, sixth paragraph, unless the element is expressly recited using the phrase "means for".

The definition of the terms "unit" or "module" as referred to herein are to be understood as constituting hardware circuitry such as a CCD, CMOS, SoC, AISC, FPGA, a processor or microprocessor (a controller) configured for a certain desired functionality, or a communication module containing hardware such as transmitter, receiver or transceiver, or a non-transitory medium comprising machine executable code that is loaded into and executed by hardware for operation, in accordance with statutory subject matter under 35 U.S.C. § 101 and do not constitute software per se.

Although a few embodiments of the present invention have been shown and described, it would be appreciated by those skilled in the art that changes may be made in these embodiments without departing from the principles and spirit of the present invention, the scope of which is defined in the claims and their equivalents.

What is claimed is:

1. An X-ray imaging apparatus configured to acquire an X-ray image by compressing an object, comprising:
    an X-ray source configured to generate X-rays that irradiate the object;
    an X-ray detector configured to detect X-rays that passed through the object and generate an electrical signal based on the detected X-rays, and the X-ray detector includes an object contact unit having a surface configured to make contact with the object; and
    a paddle arranged between the X-ray source and the X-ray detector, the paddle being vertically adjustable with respect to the X-ray source and X-ray detector so as to compress the object placed on the object contact unit,
    wherein the paddle comprises a supporting member including a rotary shaft formed to protrude toward an inside of the paddle, a pressure member coupled to the supporting member at the rotary shaft to compress the object, and at least one adjustment member elastically disposed between the supporting member and the pressure member to regulate rotation of the pressure member about the rotary shaft according to a shape of the object, when the pressure member compresses the object, the at least one adjustment member separated from the pressure member.

2. The X-ray imaging apparatus of claim 1, wherein the at least one adjustment member regulates the rotation of the pressure member by using an elastic force.

3. The X-ray imaging apparatus of claim 1, wherein the pressure member performs at least one motion from among:
    yawing motion of rotation with respect to a first axis substantially in parallel with an elevation direction of the paddle,
    rolling motion of rotation with respect to a second axis substantially perpendicular to the first axis to face the object, and
    pitching motion of rotation with respect to a third axis substantially perpendicular to the first axis and the second axis.

4. The X-ray imaging apparatus of claim 3, wherein the at least one adjustment member connects the pressure member to the supporting member so that the pressure member performs at least one motion of pitching motion, rolling motion, and yawing motion.

5. The X-ray imaging apparatus of claim 1, wherein the supporting member comprises a plurality of arms disposed to face both opposite sides of the pressure member.

6. The X-ray imaging apparatus of claim 5, wherein the at least one adjustment member comprises a first elastic member configured to connect the pressure member and the plurality of arms to be tensioned in a rotary direction of the pressure member.

7. The X-ray imaging apparatus of claim 6, wherein in the plurality of arms, an interference protrusion protrudes inward of the paddle in parallel with the rotary shaft, wherein an interference protrusion is inserted into an interference hole formed on opposite sides of the pressure member facing the plurality of arms, the interference protrusion limiting a rotary movement of the pressure member.

8. The X-ray imaging apparatus of claim 1, wherein the pressure member comprises a slit formed along at least one side of the pressure member to allow the pressure member to be elastically deformed when an external force is applied to the pressure member.

9. An X-ray imaging apparatus comprising:
    an X-ray source configured to generate X-rays that irradiate an object;
    an X-ray detector that detects X-rays that have passed through an object and generates an electrical signal based on the detected X-rays; and
    a paddle configured to be vertically adjustable with respect to the X-ray source and the X-ray detector to compress the object during an X-ray procedure of the object,
    wherein the paddle comprises a supporting member, a pressure member configured to compress the object and rotatably coupled to the supporting member via at least one elastic member separated from the pressure member, the at least one elastic member configured to regulate rotation of the pressure member with respect to the supporting member when the object is undergoing compression and an elastic force is applied to the object, and
    wherein the at least one elastic member includes a first end coupled to the supporting member and a second end coupled to the pressure member, the second end being opposite to the first end.

10. The X-ray imaging apparatus of claim 9, wherein the at least one elastic member comprises at least one of a spring, rubber and silicon.

11. The X-ray imaging apparatus of claim 9, wherein the pressure member performs at least one motion from among:
    a yawing motion of rotation with respect to a first axis in parallel with an elevation direction of the paddle,
    a rolling motion of rotation with respect to a second axis perpendicular to the first axis toward the object, and
    a pitching motion of rotation with respect to a third axis perpendicular to the first axis and the second axis.

12. The X-ray imaging apparatus of claim 9, wherein the at least one elastic member is arranged between the pressure member and the supporting member.

13. The X-ray imaging apparatus of claim 9, wherein the at least one elastic member is disposed on a lateral side of the pressure member to connect the pressure member to the supporting member.

14. The X-ray imaging apparatus of claim 13, wherein the supporting member comprises a plurality of arms disposed to face opposite sides of the pressure member, and provided with a rotary shaft that protrudes toward the inside of the paddle so that the pressure member performs a rotary movement while being coupled to the supporting member.

15. The X-ray imaging apparatus of claim 14, wherein the at least one elastic member connects the pressure member and the plurality of arms to be tensioned in a rotary direction of the pressure member.

16. The X-ray imaging apparatus of claim 15, wherein the at least one elastic member comprises a first elastic unit installed in a lateral side of the pressure member, and a second elastic unit installed in another lateral side of the pressure member that corresponds to the first elastic unit, wherein the first elastic unit and the second elastic unit are independently tensioned so that the pressure member applies uniform compression force according to a shape of the object.

17. The X-ray imaging apparatus of claim 15, wherein in the plurality of arms, an interference protrusion extends toward the inside of the paddle substantially in parallel with the rotary shaft, wherein the interference protrusion is inserted into an interference hole that is formed on opposite sides of the pressure member facing the plurality of arms, the interference protrusion limits the rotary of the pressure member.

18. The X-ray imaging apparatus of claim 9, wherein a slit is formed along at least one side of the pressure member to allow the pressure member to be elastically deformed when an external force is applied to the pressure member, and a slit cover detachably coupled to the slit and having an elastic material.

* * * * *